(12) United States Patent
Gruenbacher et al.

(10) Patent No.: US 9,636,430 B2
(45) Date of Patent: May 2, 2017

(54) MICROFLUIDIC DELIVERY SYSTEM AND CARTRIDGE HAVING AN OUTER COVER

(71) Applicant: The Procter & Gamble Company, Cincinnati, OH (US)

(72) Inventors: Dana Paul Gruenbacher, Fairfield, OH (US); Martin Diehl, Bad Vilbel (DE); Jannik Scheele, Frankfurt (DE); Joseph Edward Scheffelin, San Diego, CA (US); Uwe Schober, Glashuetten-Schlossborn (DE)

(73) Assignee: The Procter & Gamble Company, Cincinnati, OH (US)

( * ) Notice: Subject to any disclaimer, the term of this patent is extended or adjusted under 35 U.S.C. 154(b) by 68 days.

(21) Appl. No.: 14/855,653

(22) Filed: Sep. 16, 2015

(65) Prior Publication Data

US 2017/0072084 A1   Mar. 16, 2017

(51) Int. Cl.
| | | |
|---|---|---|
| *A61L 9/14* | (2006.01) | |
| *B01F 3/04* | (2006.01) | |
| *A61L 9/03* | (2006.01) | |
| *A61L 9/12* | (2006.01) | |
| *B05B 17/06* | (2006.01) | |
| *B05B 17/00* | (2006.01) | |

(52) U.S. Cl.
CPC ............... *A61L 9/032* (2013.01); *A61L 9/122* (2013.01); *A61L 9/14* (2013.01); *B01F 3/0407* (2013.01); *B01F 3/04021* (2013.01); *B01F 3/04085* (2013.01); *B05B 17/0646* (2013.01); *B05B 17/0684* (2013.01)

(58) Field of Classification Search
CPC .... B01F 3/04; B01F 3/04021; B01F 3/04049; B01F 3/0407; B01F 3/04085; B05B 1/24; B05B 17/0646; B05B 17/0684; A61L 9/14; A61L 9/03

USPC ............ 261/142, 107, 30, DIG. 65, DIG. 88, 261/DIG. 89
See application file for complete search history.

(56) References Cited

U.S. PATENT DOCUMENTS 5,975,675 A   11/1999  Kim
6,261,347 B1   7/2001  Moreland
(Continued)

FOREIGN PATENT DOCUMENTS

CN         1223637 C    10/2005
CN       101 020 073 A    8/2007
(Continued)

OTHER PUBLICATIONS

U.S. Appl. No. 14/855,662, filed Sep. 16, 2015, Gruenbacher, et al.
U.S. Appl. No. 14/855,677, filed Sep. 16, 2015, Gruenbacher, et al.
PCT Search Report dated Jun. 19, 2015; PCT/US2015/036546, 5 Pages.

(Continued)

*Primary Examiner* — Robert A Hopkins
(74) *Attorney, Agent, or Firm* — Abbey A. Lopez

(57) ABSTRACT

A cartridge for a microfluidic delivery system is defined by a longitudinal axis. The cartridge includes a reservoir for containing a fluid composition. The cartridge also includes a nozzle operatively connected with the reservoir. The nozzle is in fluid communication with the reservoir for releasing the fluid composition. The cartridge includes an outer cover operatively connected with the reservoir. The outer cover comprises an orifice that is adjacent to the nozzle. An air flow path is formed by a gap between the reservoir and the outer cover.

20 Claims, 22 Drawing Sheets

(56) References Cited

U.S. PATENT DOCUMENTS

| | | |
|---|---|---|
| 6,325,475 B1 | 12/2001 | Hayes et al. |
| 6,371,451 B1 | 4/2002 | Choi |
| 7,367,661 B2 | 5/2008 | Hess et al. |
| 7,499,632 B2 * | 3/2009 | Granger .............. A01M 1/2033 392/386 |
| 8,020,573 B2 | 9/2011 | Lamers et al. |
| 8,870,090 B2 * | 10/2014 | Feriani ................ B05B 17/0646 239/102.1 |
| 2002/0192255 A1 | 12/2002 | Schiavo et al. |
| 2004/0032468 A1 | 2/2004 | Killmeier et al. |
| 2006/0065755 A1 | 3/2006 | Sugita et al. |
| 2010/0154790 A1 | 6/2010 | Merassi et al. |
| 2014/0078229 A1 | 3/2014 | Jackson et al. |
| 2015/0367013 A1 | 12/2015 | Gruenbacher et al. |
| 2015/0367014 A1 | 12/2015 | Gruenbacher et al. |
| 2015/0367016 A1 | 12/2015 | Gruenbacher et al. |
| 2015/0367356 A1 | 12/2015 | Gruenbacher et al. |
| 2015/0368001 A1 | 12/2015 | Gruenbacher et al. |

FOREIGN PATENT DOCUMENTS

| | | |
|---|---|---|
| GB | 2410468 A | 3/2005 |
| JP | 2005185366 A | 7/2005 |
| JP | 2005224504 A | 8/2005 |
| JP | 2007054446 A | 3/2007 |
| KR | 100238582 B1 | 1/2000 |
| WO | WO 2004/044552 A2 | 5/2004 |
| WO | WO 2014/043424 A1 | 3/2014 |

OTHER PUBLICATIONS

PCT Search Report dated Sep. 17, 2015; PCT/US2015/036549, 11 Pages.

PCT Search Report dated Sep. 18, 2015; PCT/US2015/036551, 9 pages.

PCT Search Report dated Oct. 16, 2015; PCT/US2015/036548, 9 Pages.

* cited by examiner

MICROFLUIDIC DELIVERY SYSTEM AND CARTRIDGE HAVING AN OUTER COVER

FIELD

The present disclosure generally relates to systems for delivering a fluid composition into the air, and, more particularly, relates to microfluidic delivery systems and cartridges for delivering fluid compositions into the air using a die.

BACKGROUND

Various systems exist to deliver fluid compositions, such as perfume compositions, into the air by energized (i.e. electrically/battery powered) atomization. In addition, recent attempts have been made to deliver fluid compositions, such as perfume compositions, into the air using microfluidic delivery technology such as thermal and piezo inkjet heads.

When using microfluidic delivery technology to deliver fluid compositions, especially when delivering the fluid compositions into the air, proper fill of the atomized fluid composition into the surrounding space may be important.

One method used to increase room fill includes the use of a fan in combination with a microfluidic delivery device, such a thermal or piezo inkjet head. A fan may be placed on the opposite side of the inkjet head from where the fluid composition is dispensed to help force the fluid composition into the air. However, even with the use of a fan, there is still a need for increased air flow to help deliver the atomized fluid composition into the air with sufficient force to fill a room. Higher powered fans can be to provide increased air flow, but would increase the energy consumption of the device.

Thus, it would be beneficial to provide a device that delivers atomized fluid composition into the air with sufficient force to fill a room or space with the fluid composition.

SUMMARY

Aspects of the present disclosure include a cartridge for a microfluidic delivery system. The cartridge has a longitudinal axis. The cartridge comprises a reservoir for containing a fluid composition. The cartridge comprises a nozzle operatively connected with the reservoir. The nozzle is in fluid communication with the reservoir for releasing the fluid composition. The cartridge comprises an outer cover operatively connected with the reservoir. The outer cover comprises an orifice that is adjacent to the nozzle. An air flow path is formed by a gap between the reservoir and the outer cover.

Aspects of the present disclosure also include a cartridge for a microfluidic delivery system. The cartridge has a longitudinal axis. The cartridge comprises a reservoir for containing a fluid composition. The reservoir comprises a top portion, a base portion opposing the top portion, and at least one sidewall extending between and connecting the top and base portions. The cartridge comprises a nozzle operatively connected with the reservoir. The nozzle is in fluid communication with the reservoir for releasing the fluid composition. The cartridge comprises an outer cover operatively connected with the reservoir. The outer cover comprises a top and a skirt that extends from the top of the outer cover and at least partially overlaps with the sidewall of the reservoir along the longitudinal axis. The top of the outer cover comprises an orifice. An air flow path is formed between the outer cover and the reservoir and extends from the skirt to the orifice.

Aspects of the present disclosure also include a cartridge for a microfluidic delivery system. The cartridge comprises a reservoir containing a fluid composition to be dispensed from at least one nozzle. The cartridge also comprises an outer cover connected with the reservoir. The outer cover has a top with an orifice disposed adjacent to the nozzle and a skirt extending from the top. At least one of the reservoir and the outer cover comprising electrical contacts that are electrically connectable with the microfluidic delivery system.

Aspects of the present disclosure also include a microfluidic delivery system comprising a housing having a base, at least one sidewall connected with the base, and an opening for receiving a cartridge at least partially within the housing. The housing comprises an air inlet. The microfluidic delivery system comprises a fan in fluid communication with the housing and a cartridge releasably and electrically connectable with the housing. The cartridge has a longitudinal axis. The cartridge comprises a reservoir containing a fluid composition to be dispensed from at least one nozzle. The cartridge also comprises an outer cover connected with the reservoir. The outer cover has a top with an orifice disposed adjacent to the nozzle and a skirt extending from the top. The outer cover comprises an orifice that is disposed adjacent to the nozzle. An air flow path is formed by a gap between the reservoir and the outer cover.

DETAILED DESCRIPTION

Figure 1:
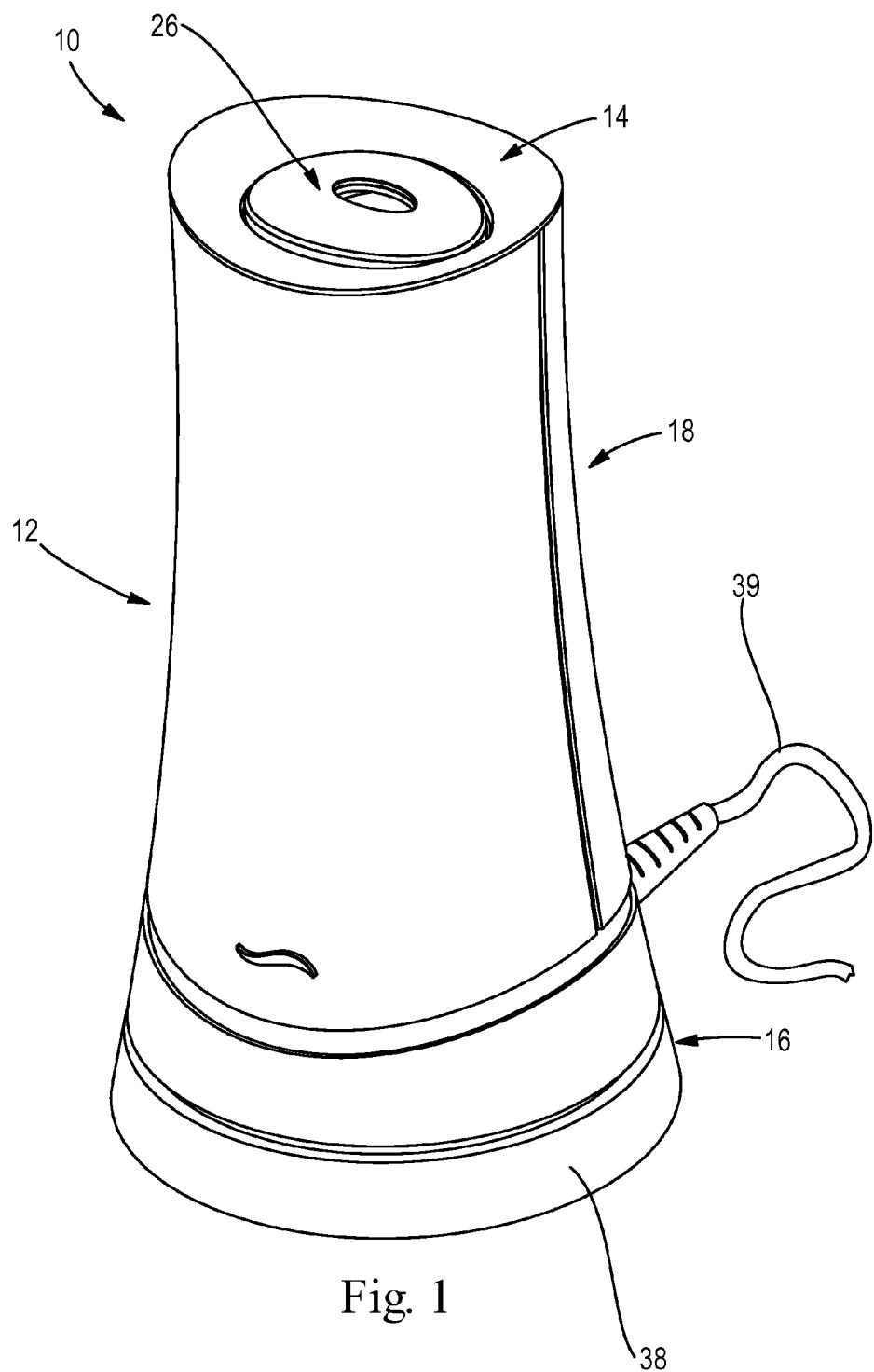
FIG. 1 is a perspective view of a microfluidic delivery system including a housing having a cartridge disposed therein and a charger for recharging rechargeable batteries used to power the microfluidic delivery system.

The present disclosure provides a microfluidic delivery system comprising a cartridge having a microfluidic delivery member and methods for delivering fluid compositions into the air.

The microfluidic delivery system of the present disclosure may include a housing and a cartridge. The cartridge may be fixed with the housing, removably connectable with the housing, and/or replaceable, and may be disposed at least partially within the housing. The cartridge may comprise a reservoir for containing a volatile composition, a microfluidic delivery member, and a fluid transport member disposed within the reservoir and configured to deliver a fluid composition from within the reservoir to the microfluidic delivery member. The microfluidic delivery member may be configured to dispense the fluid composition into the air. The cartridge is electrically connectable with the housing.

The reservoir may be defined by a top portion, a base portion, and a sidewall(s) connecting and extending between the top portion and the base portion. The microfluidic delivery member may be connected with the reservoir.

The cartridge may include an outer cover. The outer cover may be defined by an interior and an exterior. The outer cover may include a top that is defined by a perimeter. The top includes an orifice. The top of the outer cover may substantially cover the top portion of the reservoir. The orifice may be disposed adjacent to the die, and, for example, may be at least partially aligned, or fully aligned therewith. The outer cover is connected with the reservoir such that a gap is formed between the outer cover and the reservoir, forming an air flow path between the outer cover and the reservoir.

The outer cover may include a skirt that extends from the perimeter of the top toward the reservoir. The skirt may surround at least a portion of the sidewall(s) of the reservoir. The skirt may be configured such that air is able to flow longitudinally adjacent to the sidewall(s) of the reservoir. The air flow path preferably extends around all or most all of the reservoir. For example, it may be desirable for the air flow path to extend at least about 300 degrees around the reservoir, about 350 degrees about the reservoir, or about 360 degrees about the reservoir.

While the below description describes the microfluidic delivery system comprising a housing and a cartridge, both having various components, it is to be understood that the microfluidic delivery system is not limited to the construction and arrangement set forth in the following description or illustrated in the drawings. The microfluidic delivery system and cartridge of the present disclosure are applicable to other configurations or may be practiced or carried out in various ways. For example, the components of the housing may be located on the cartridge and vice-versa. Further, the housing and cartridge may be configured as a single unit versus constructing a cartridge that is separable from the housing as described in the following description. Moreover, the cartridge may be used with various devices for delivering fluid composition into the air or onto a target surface.

Housing

Figure 2:
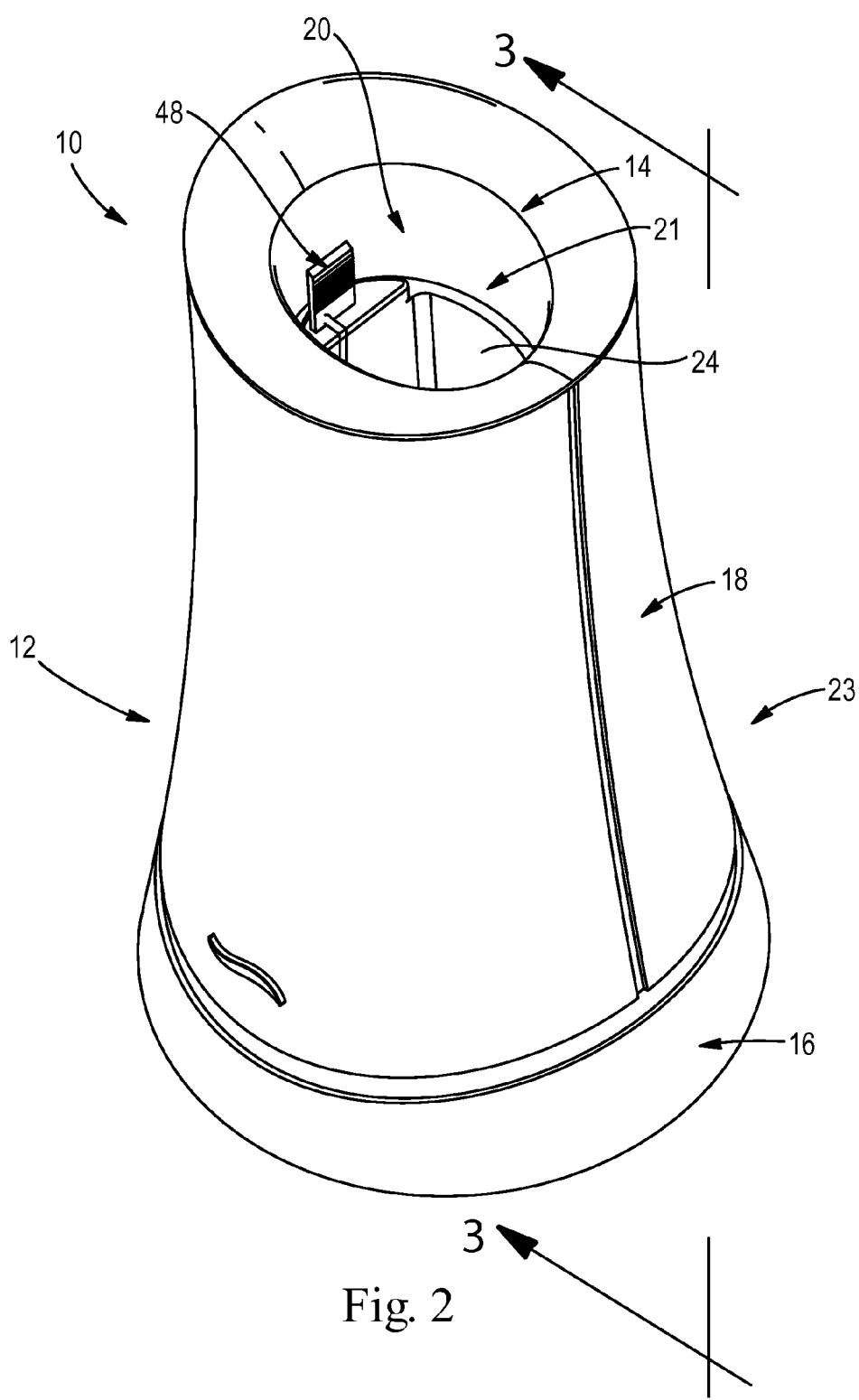
FIG. 2 is a perspective view of the housing of the microfluidic delivery system of FIG. 1 without a charger or cartridge connected therewith.
Figure 3:
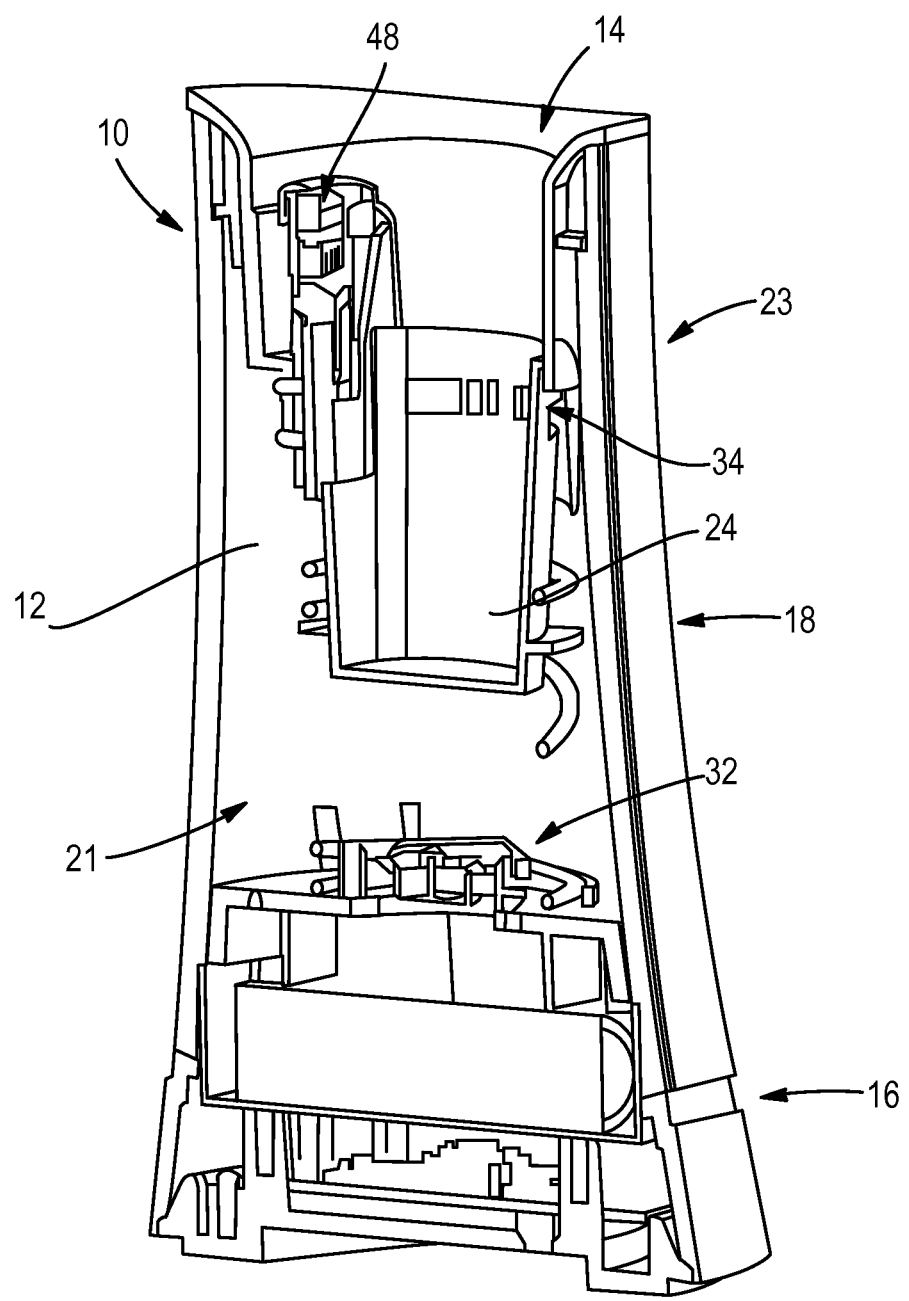
FIG. 3 is a sectional view of FIG. 2 taken along line 3-3.

With reference to FIGS. 1-3, the microfluidic delivery system 10 may include a housing 12. The housing 12 may be constructed from a single component or have multiple components that are combined to form the housing 12. The housing 12 may be defined by an interior 21 and an exterior 23. The housing 12 may be comprised of an upper portion 14, a lower portion 16, and a body portion 18 that extends between and connects the upper portion 14 and the lower portion 16.

Figure 4:
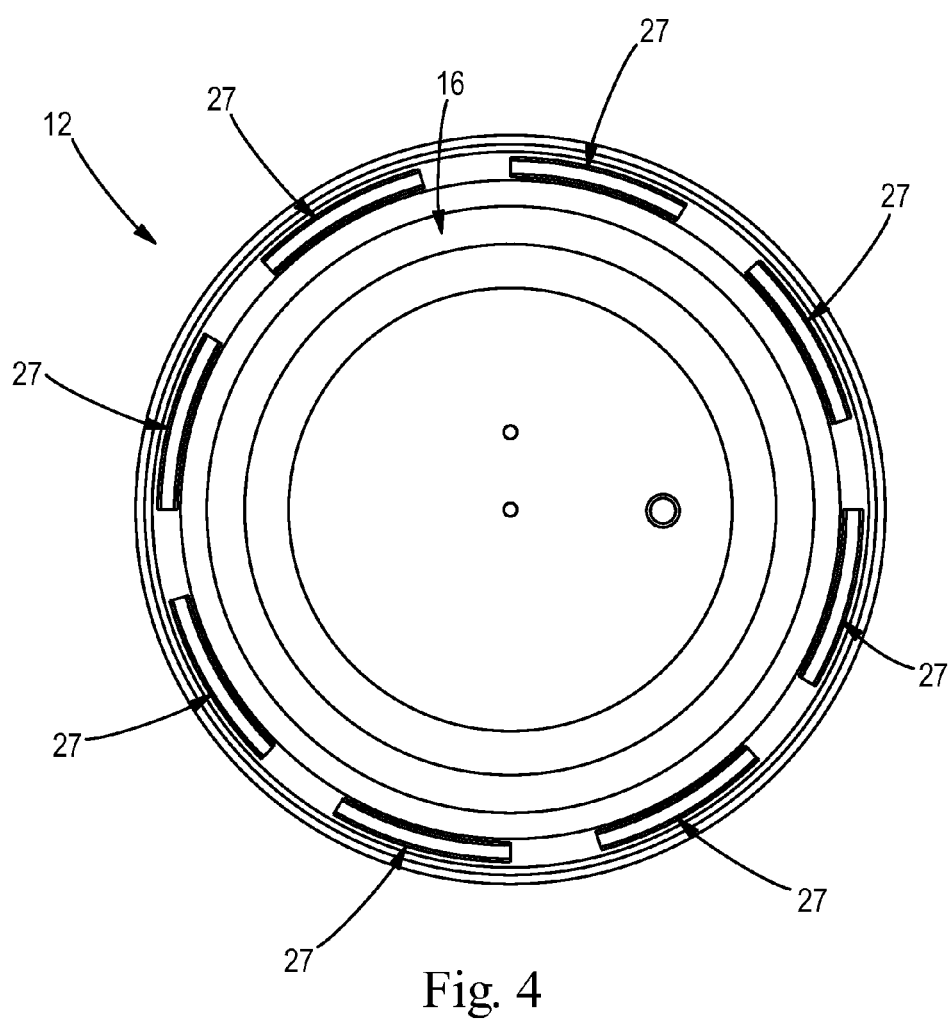
FIG. 4 is a bottom, plan view of the housing of FIG. 2.

The housing 12 may include an opening 20 in the upper portion 14 of the housing 12 and a holder 24 for receiving and holding the cartridge 26 in the housing 12. The cartridge 26 may be received into the upper portion 14 of the housing 12. An air flow channel 34 may be formed between the holder 24 and the upper portion 14 of the housing 12. With reference to FIG. 4, the housing 12 may comprise one or more air inlets 27. The air inlets 27 may be positioned in the lower portion 16 of the housing, as shown in FIG. 4 for illustrative purposes only, or may be formed in the body portion 18 of the housing.

The microfluidic delivery system 10 may comprise a fan 32 to assist in driving room-fill and/or to help avoid deposition of larger droplets from landing on surrounding surfaces of the device that could damage the surface. The fan 32, for example, may be disposed at least partially within the interior 21 of the housing 12 and may be positioned between the holder 24 and the lower portion 16 of the housing 12. However, the fan may be configured and arranged in any other way suitable for the desired use. An exemplary fan includes a 5V 25×25×8 mm DC axial fan (Series 250, Type255N from EBMPAPST), that is capable of delivering about 10 to about 50 liters of air per minute (l/min), or about 15 l/min to about 25 l/min. As will be discussed in more detail below, the fan 32 pulls air from the air inlet(s) 27 into the housing 12 and directs the air up through the air flow channels 34 toward the cartridge 26. The air velocity exiting the opening 20 may be in the range of about 1 meter per second (m/s) to about 5 m/s, or about 1.5 m/s to about 2.5 m/s.

The microfluidic delivery system 10 may be in electrical communication with a power source. The power source may be located in the interior 21 of the housing 12, such as a disposable battery or a rechargeable battery. Or, the power source may be an external power source such as an electrical outlet that connects with a power cord 39 connected with the housing 12. The housing 12 may include an electrical plug that is connectable with an electrical outlet. The microfluidic delivery system may be configured to be compact and easily portable. As such, the power source may include rechargeable or disposable batteries. The microfluidic delivery system may be capable for use with electrical sources as 9-volt batteries, conventional dry cells such as "A", "AA", "AAA", "C", and "D" cells, button cells, watch batteries, solar cells, as well as rechargeable batteries with recharging base.

With reference to FIG. 1, the microfluidic delivery system 10 may be powered by rechargeable batteries disposed within the interior 21 of the housing. The rechargeable batteries may be charged using a charger 38. The charger 38 may include an power cord 39 that connects with an external power source, such as an electrical outlet or battery terminals. The charger 38 may receive the housing 12 to charge the batteries. As will be discussed in more detail below, electrical contacts 48 disposed on the interior 21 of the housing couple with the internal or external power source and couple with electrical contacts on the microfluidic delivery member of the cartridge to power the die. The housing 12 may include a power switch on exterior 23 of the housing 12.

Figure 5:
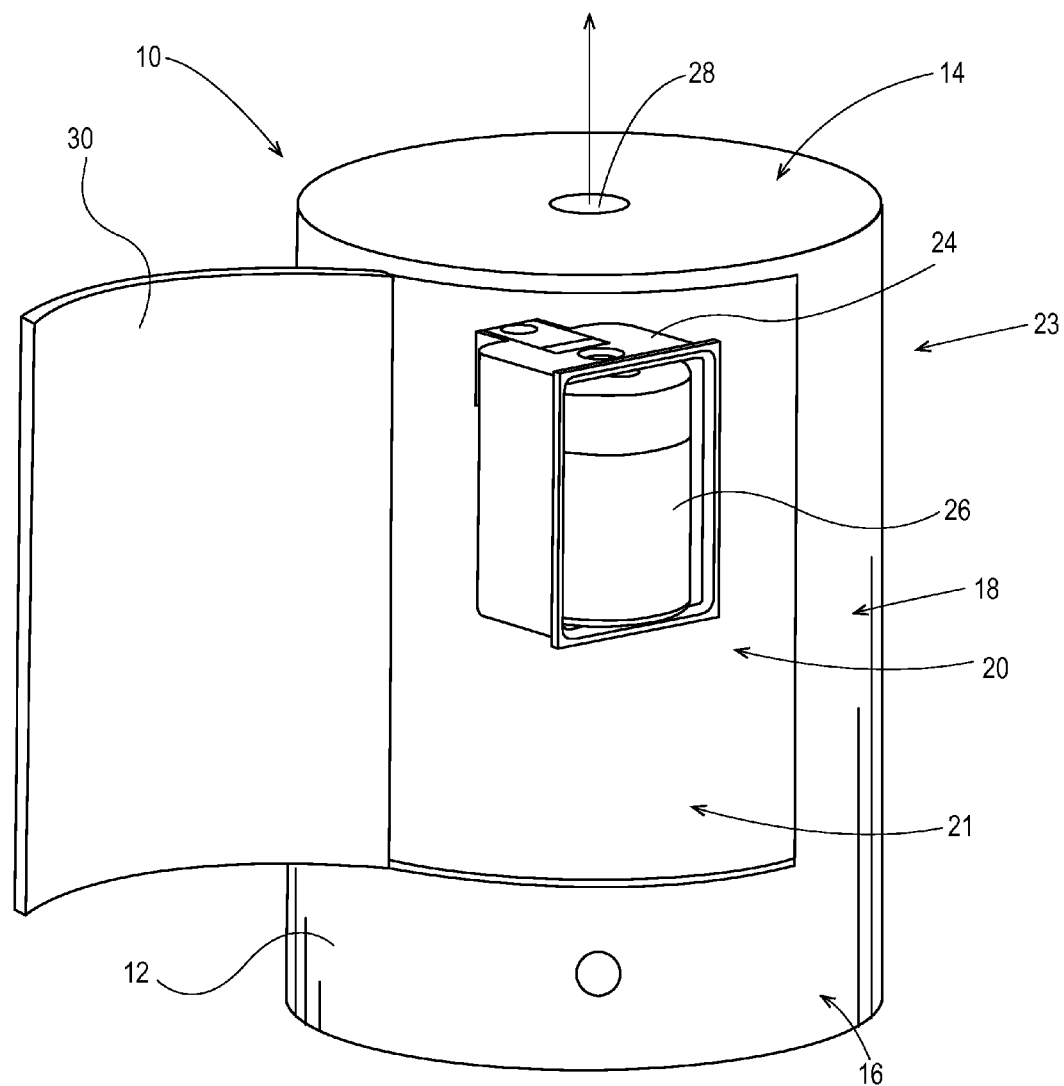
FIG. 5 is a schematic, perspective view of a housing having a cartridge disposed therein, and comprising a door for accessing the interior of the housing.
Figure 6:
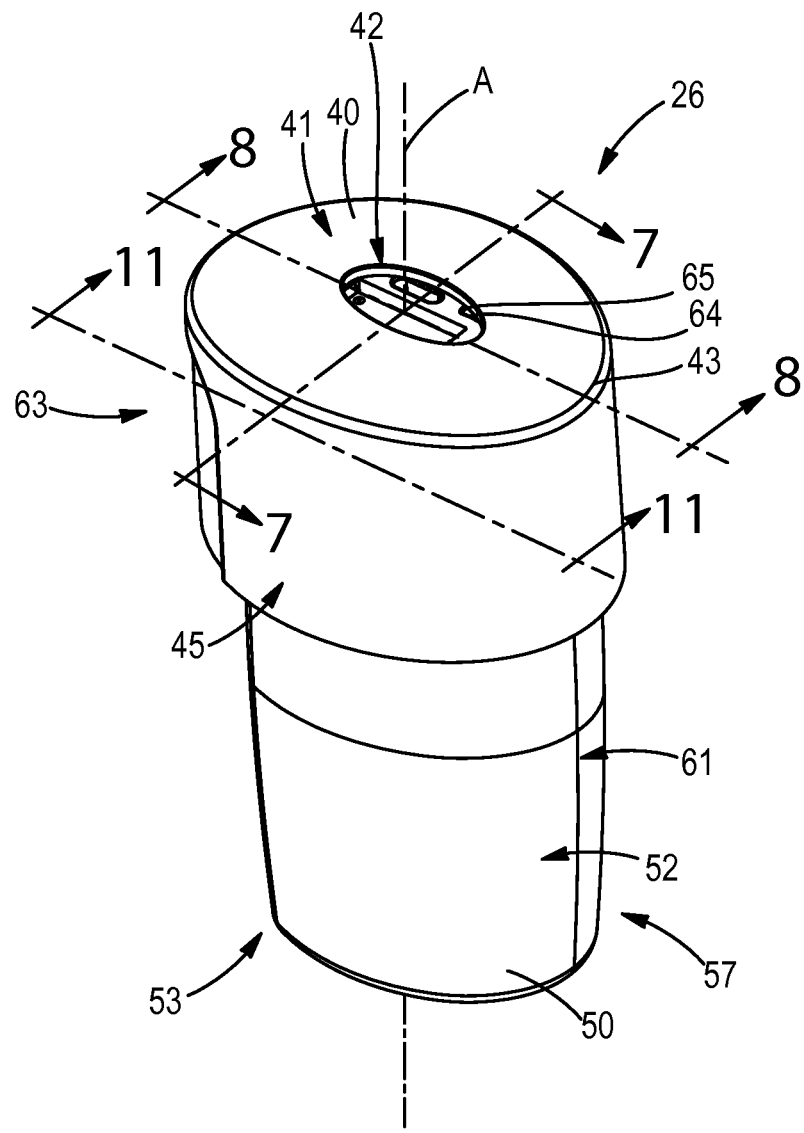
FIG. 6 is a perspective view of a cartridge having a reservoir and an outer cover.
Figure 7:
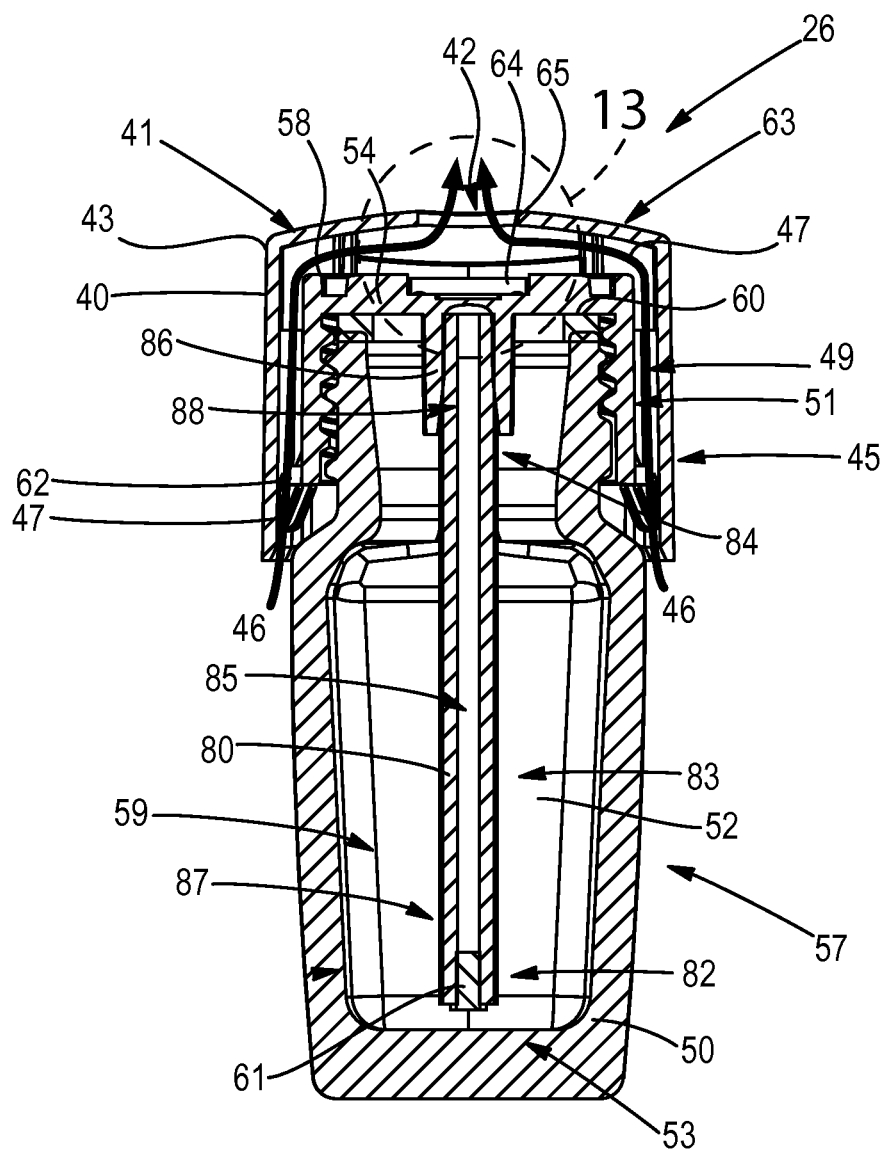
FIG. 7 is a sectional view of FIG. 6 taken along line 7-7.

With reference to FIG. 5, the opening 20 may be disposed in the upper or body portion 14 or 18 of the housing 12. The housing 12 may include a door 30 or structure to cover the opening 20. The cartridge 26 may slide in through the opening in the body portion 18 of the housing 12. The housing 12 may include air outlet 28 that places an environment on the exterior 23 of the housing 12 in fluid communication with the interior 21 of the housing 12. The door 30 may rotate to provide access to the air outlet 28. However, it is to be appreciated that the door or covering may be configured in various different ways. The door 30 may form a substantially air tight connection with the remainder of the housing 12 such that pressurized air in the interior 21 of the housing 12 does not escape through any gaps between the door 30 and the housing.

Cartridge

With reference to FIGS. 1 and 6-13, the cartridge 26 may have a longitudinal axis A and may comprise a reservoir 50 for containing a fluid composition 52. The cartridge 26 may include a die 92 and a fluid transport member 80. The fluid transport member 80 may be configured to deliver fluid composition from the reservoir 50 to the die 92. The die 92 may be configured to dispense the fluid composition into the air or onto a target surface. The cartridge 26 may include an outer cover 40 that is mechanically connected with the reservoir 50. The outer cover 40 may include an orifice 42 that at least partially exposes the die 92. The orifice 42 may be adjacent to the die 92, and may be at least partially aligned with the die 92. An air flow path 46 may be formed in a gap between the reservoir 50 and the outer cover 40. When the cartridge 26 is connected with the housing 12, at least a portion of the outer cover 40 may be visible from the exterior of the housing 12. Air pressure generated by the fan causes air to travel through the air flow path 46 and out of the orifice 42. The fluid composition 52 dispensed from the die 92 combines with the air exiting the orifice 42, helping the fluid composition 52 to be dispensed into the air and adequately fill a room or space.

As will be discussed in more detail below, when the cartridge 26 is connected with the housing 12, the fan 32 may direct air through the air flow path 46 as the die 92 dispenses a portion of fluid composition into the air, causing the fluid composition 52 to exit through the orifice 42 of the outer cover 40. The air flow from the fan 32 provides additional force to carry the dispensed fluid composition 52 into the air, which, in turn, can increase room fill, and/or decrease deposition, and/or direct the fluid composition to the desired target. It is to be appreciated that increased air flow through the air flow path 46 is associated with increased carrying of the fluid composition 52 into the air. Moreover, the size of the orifice can be adjusted in order to control the velocity of the air flowing through the orifice 42.

Reservoir

With reference to FIGS. 6-9, 11, and 12, the cartridge 26 includes a reservoir 50 for containing a fluid composition. The reservoir 50 may be configured to contain from about 5 milliliters (mL) to about 100 mL, alternatively from about 10 mL to about 50 mL, alternatively from about 15 mL to about 30 mL of fluid composition. The cartridge 26 may be configured to have multiple reservoirs, with each reservoir containing the same or a different fluid composition. The reservoir can be made of any suitable material for containing a fluid composition including glass, plastic, metal, or the like.

The reservoir 50 may be comprised of a top portion 51, a base portion 53 opposing the top portion 51, and at least one sidewall 61 connected with and extending between the top portion 51 and the base portion 53. The reservoir 50 may define an interior 59 and an exterior 57. The top portion 51 of the reservoir 50 may include an air vent 93 and a fluid outlet 90. While the reservoir 50 is shown as having a top portion 51, a base portion 53, and at least one sidewall 61, it is to be appreciated that the reservoir 50 may be configured in various different ways.

The reservoir 50, including the top portion 51, base portion 53, and sidewall(s) 61, may be configured as a single element or may be configured as separate elements that are joined together. For example, the top portion 51 or base portion 53 may be configured as a separate element from the remainder of the reservoir 50. For example, with reference to FIGS. 7 and 8, the reservoir 50 may be comprised of two elements joined together; the base portion 53 and the sidewall(s) 61 may be one element and the top portion 51 may be a separate element. The top portion 51 may be configured as a lid 54 that is mechanically connected with the sidewall(s) 61. The lid 54 may be removably or fixably connected with the sidewall(s) 61 to substantially enclose the reservoir 50. The lid 54 may be threadingly attached with the sidewall(s) 61 of the reservoir 50, or may be welded, glued, or the like with the sidewall(s) 61 of the reservoir 50.

With reference to FIGS. 7-8 and 13, the reservoir 50 may include a connection member 86 extending from the interior 59 of the reservoir 50. The connection member 86 may define a chamber 88 for receiving a portion of the second end portion 84 of the fluid transport member 80. The chamber 88 may be substantially sealed between the connection member 86 and the fluid transport member 80 to prevent air from the reservoir 50 from entering the chamber 88.

In an example configuration wherein the top portion 51 of the reservoir 50 includes a lid 54, the connection member 86 may extend from the lid 54. The lid 54 of the reservoir may be defined by an outer surface 58 and an inner surface 60. The lid 54 may include a connection member 86 extending from the inner surface 60.

The reservoir may be transparent, translucent, or opaque or any combination thereof. For example, the reservoir may be opaque with a transparent indicator of the level of fluid composition in the reservoir.

Fluid Transport Member

With reference to FIGS. 7 and 8, the cartridge 26 includes a fluid transport member 80 disposed within the interior 59 of the reservoir 50. The fluid transport member 80 may be defined by a first end portion 82, a second end portion 84, and a central portion 83. The first end portion 82 is in fluid communication with the fluid composition 52 in the reservoir 50 and the second end portion 84 is operatively connected with the connection member 86 of the reservoir 50. The second end 84 of the fluid transport member 80 is located below the microfluidic delivery member 64. The fluid transport member 80 delivers fluid composition from the reservoir 50 to the microfluidic delivery member 64. Fluid composition can travel by wicking, diffusion, suction, siphon, vacuum, or other mechanism against the force of gravity. The fluid composition may be transported to the microfluidic delivery member 64 by a gravity fed system known in the art.

The fluid transport member 80 may be configured in various ways, including in the form of a capillary tube or wicking material. The wicking material may be in the form of a metal or fabric mesh, sponge, or fibrous or porous wick that contains multiple interconnected open cells that form capillary passages to draw a fluid composition up from the reservoir to the microfluidic delivery member. Non-limiting examples of suitable compositions for the fluid transport member include polyethylene, ultra-high molecular weight polyethelene, nylon 6, polypropylene, polyester fibers, ethyl vinyl acetate, polyether sulfone, polyvinylidene fluoride, and polyethersulfone, polytetrafluroethylene, and combinations thereof. Many traditional ink jet cartridges use an open-cell polyurethane foam which can be incompatible with perfume mixtures over time (e.g. after 2 or 3 months) and can break down. The fluid transport member 80 may be free of a polyurethane foam.

The fluid transport member 80 may be a high density wick composition to aid in containing the scent of a perfume mixture. The fluid transport member may be made from a plastic material chosen from high-density polyethylene or polyester fiber. As used herein, high density wick compositions include any conventional wick material having a pore radius or equivalent pore radius (e.g. in the case of fiber based wicks) ranging from about 20 microns to about 200 microns, alternatively from about 30 microns to about 150 microns, alternatively from about 30 microns to about 125 microns, alternatively, about 40 microns to about 100 microns.

Regardless of the material of manufacture, where a wicking material is used, the fluid transport member 80 can exhibit an average pore size from about 10 microns to about 500 microns, alternatively from about 50 microns to about 150 microns, alternatively about 70 microns. The average pore volume of the wick, expressed as a fraction of the fluid transport member not occupied by the structural composition, is from about 15% to about 85%, alternatively from about 25% to about 50%. Good results have been obtained with wicks having an average pore volume of about 38%.

The fluid transport member 80 may be any shape that is able to deliver fluid composition from the reservoir 50 to the microfluidic delivery member 64. Although the fluid transport member 80 has a width dimension, such as diameter, that is significantly smaller than the reservoir 50, it is to be appreciated that the diameter of the fluid transport member 80 may be larger and may substantially fill the reservoir 50. The fluid transport member 80 can also be of variable length, such as, from about 1 mm to about 100 mm, or from about 5 mm to about 75 mm, or from about 10 mm to about 50 mm.

Figure 8:
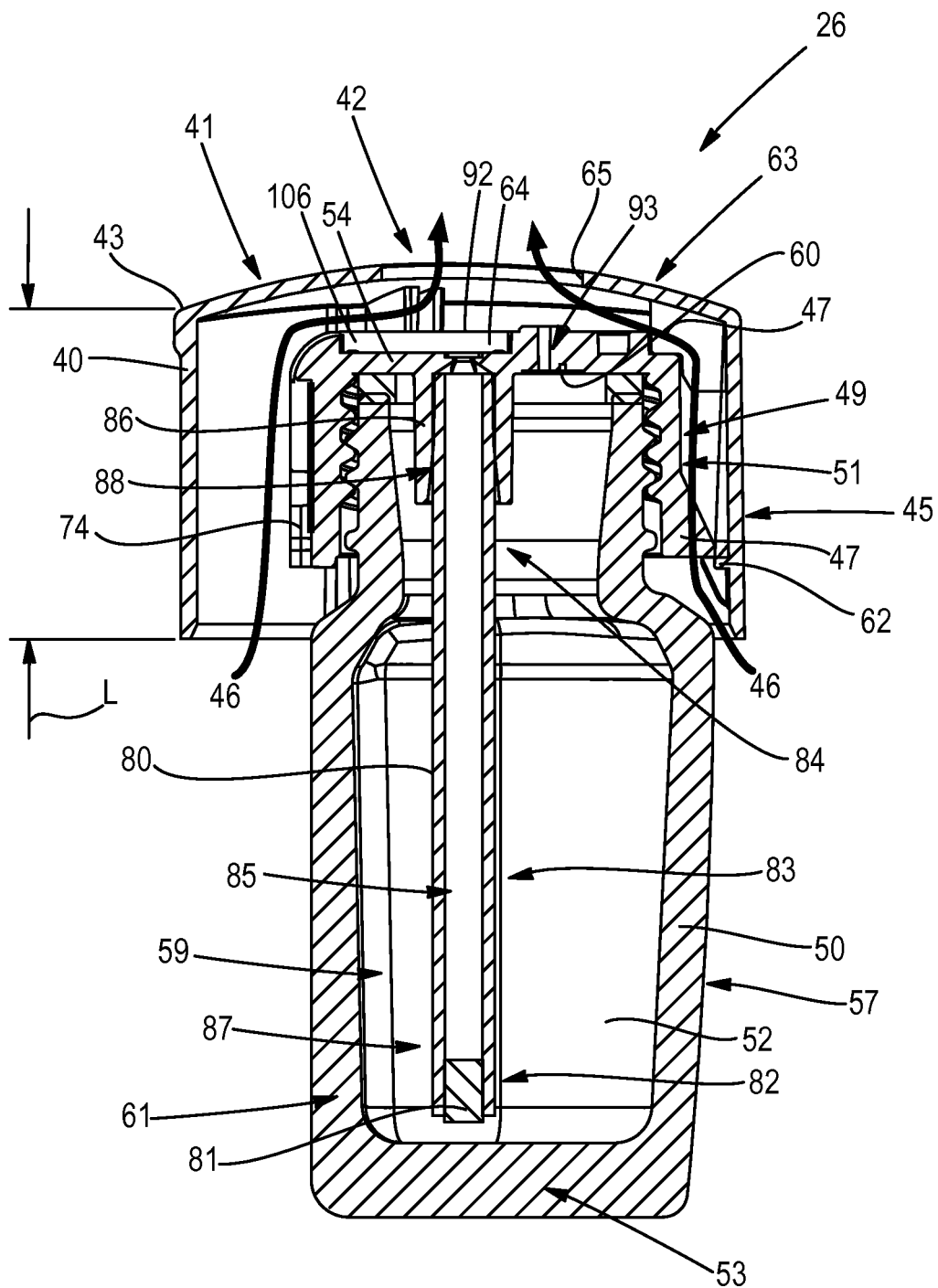
FIG. 8 is a sectional view of FIG. 6 taken along line 8-8.
Figure 9:
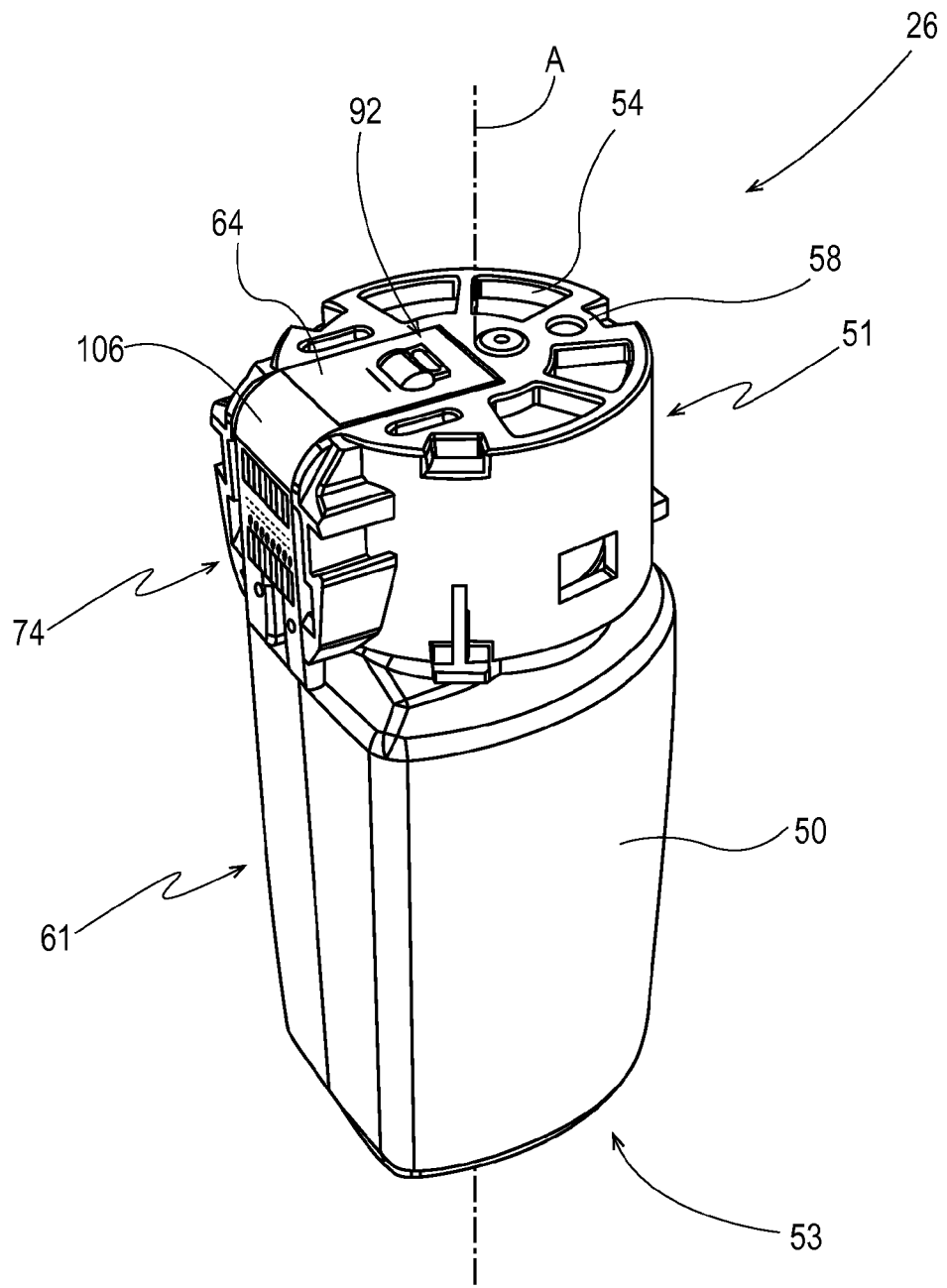
FIG. 9 is a perspective view of a cartridge with an outer cover removed to make visible a reservoir having a microfluidic delivery member with a semi-flex printed circuit board (PCB) connected therewith.
Figure 10:
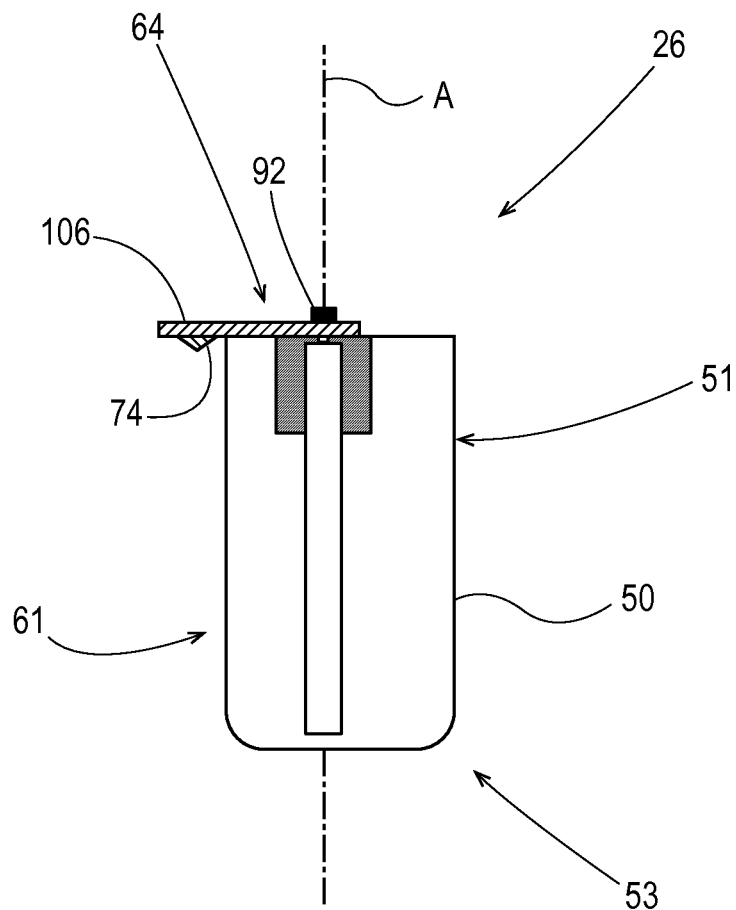
FIG. 10 is a schematic, sectional view of a cartridge with an outer cover removed to make visible a reservoir having a microfluidic delivery member with a rigid PCB connected therewith.

With reference to FIG. 8, if the fluid transport member 80 is configured as a capillary tube, the fluid transport member 80 may include a restriction member 81. The restriction member 81 prevents or minimizes the chance of an air bubble from the reservoir 50 passing through the fluid transport member 80 and blocking the nozzles 130 of the die 92. An exemplary restriction member is described in U.S. Patent Application entitled, "MICROFLUIDIC DELIVERY SYSTEM AND CARTRIDGE", Ser. No. 14/855,677, filed on Sep. 16, 2015.

Microfluidic Delivery Member

With reference to FIGS. 7-10 and 14A-15B, the microfluidic delivery system 10 may comprise a microfluidic delivery member 64 that utilizes aspects of ink-jet print head systems, and more particularly, aspects of thermal or piezo ink-jet print heads. The microfluidic delivery member 64 may be connected with the top portion 51 and/or sidewall 61 of the reservoir 50 of the cartridge 26.

In a "drop-on-demand" ink-jet printing process, a fluid composition is ejected through a very small orifice of a diameter typically about 5-50 microns, or between about 10 and about 40 microns, in the form of minute droplets by rapid pressure impulses. The rapid pressure impulses are typically generated in the print head by either expansion of a piezoelectric crystal vibrating at a high frequency or volatilization of a volatile composition (e.g. solvent, water, propellant) within the ink by rapid heating cycles. Thermal ink-jet printers employ a heating element within the print head to volatilize a portion of the composition that propels a second portion of fluid composition through the orifice nozzle to form droplets in proportion to the number of on/off cycles for the heating element. The fluid composition is forced out of the nozzle when needed. Conventional ink-jet printers are more particularly described in U.S. Pat. Nos. 3,465,350 and 3,465,351.

The microfluidic delivery member 64 may be in electrical communication with a power source and may include a printed circuit board ("PCB") 106 and a die 92 that is in fluid communication with the fluid transport member 80.

Figure 14A:
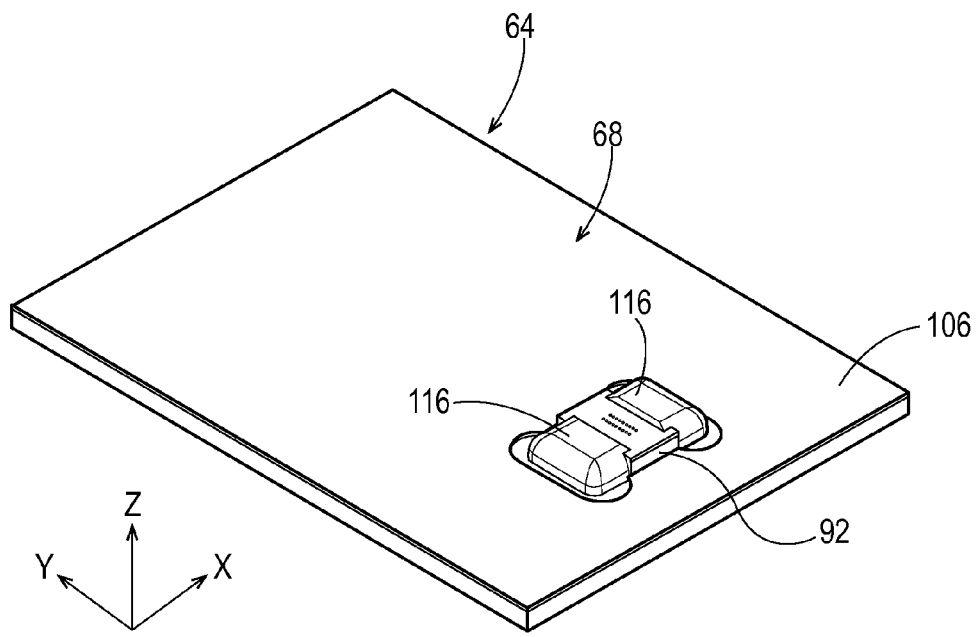
FIG. 14A is a top, perspective view of a microfluidic delivery member having a rigid PCB.
Figure 14B:
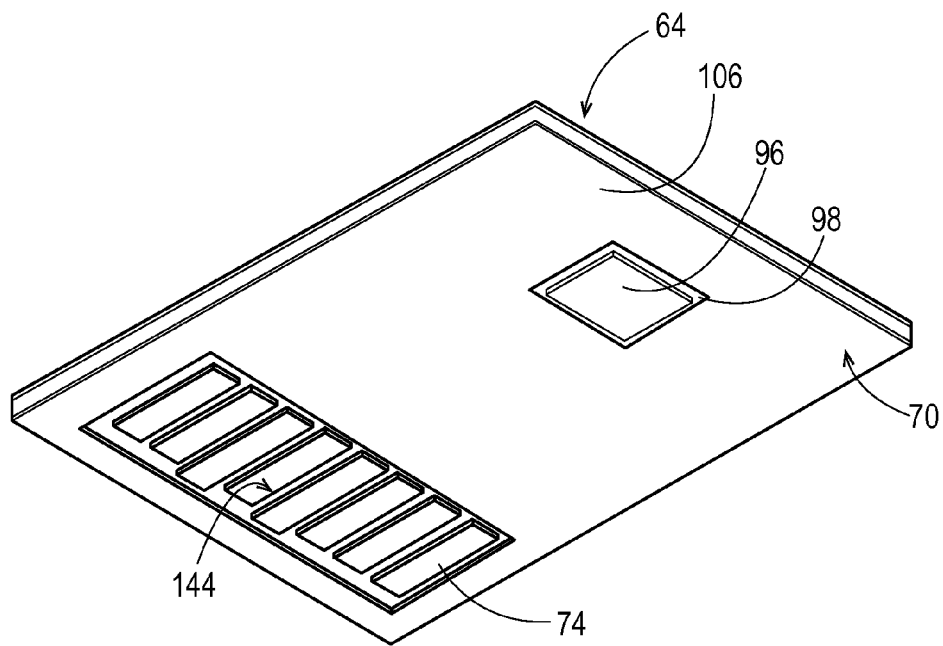
FIG. 14B is a bottom, perspective view of a microfluidic delivery member having a rigid PCB.
Figures 15A, 15B:
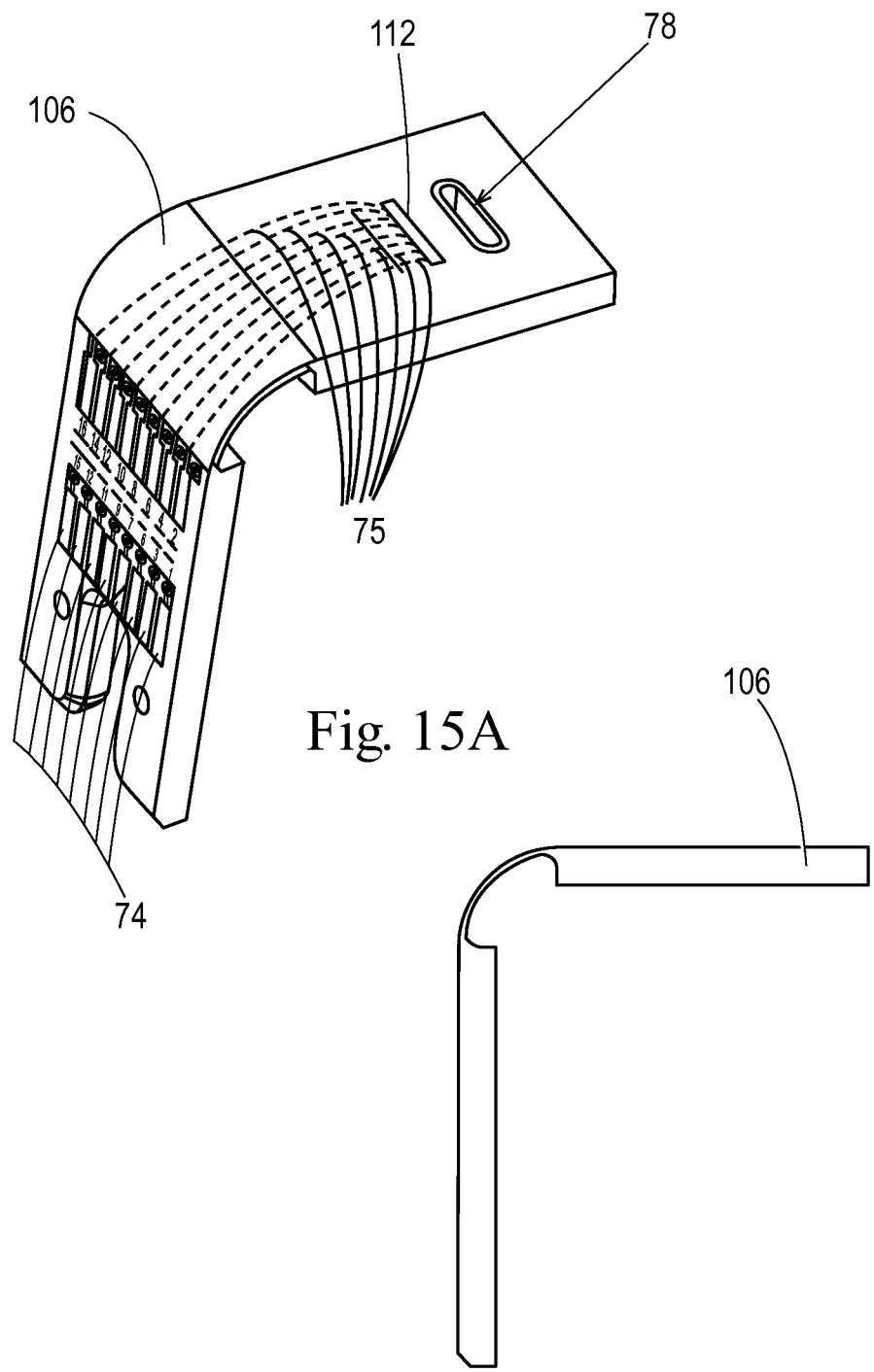
FIG. 15A is a perspective view of a semi-flex PCB for a microfluidic delivery member.
FIG. 15B is side, elevation view of a semi-flex PCB for a microfluidic delivery member.

The PCB 106 may be a rigid planar circuit board, such as shown in FIGS. 14A and 14B for illustrative purposes only; a flexible PCB; or a semi-flex PCB, such as shown in FIGS. 15A and 15B for illustrative purposes only. The semi-flex PCB shown in FIGS. 15A and 15B may include a fiberglass-epoxy composite that is partially milled in a portion that allows a portion of the PCB 106 to bend. The milled portion may be milled to a thickness of about 0.2 millimeters. The PCB 106 has upper and lower surfaces 68 and 70.

The PCB 106 may be of a conventional construction. It may comprise a ceramic substrate. It may comprise a fiberglass-epoxy composite substrate material and layers of conductive metal, normally copper, on the top and bottom surfaces. The conductive layers are arranged into conductive paths through an etching process. The conductive paths are protected from mechanical damage and other environmental effects in most areas of the board by a photo-curable polymer layer, often referred to as a soldermask layer. In selected areas, such as the liquid flow paths and wire bond attachment pads, the conductive copper paths are protected by an inert metal layer such as gold. Other material choices could be tin, silver, or other low reactivity, high conductivity metals.

Still referring to FIGS. 14A-16, the PCB 106 may include all electrical connections—the contacts 74, the traces 75, and the contact pads 112. The contacts 74 and contact pads 112 may be disposed on the same side of the PCB 106, or may be disposed on different sides of the PCB. For example, as shown in FIGS. 14A and 14B, the contacts 74 may be disposed on opposite sides of the PCB 106. The contacts 74 may be disposed on the lower surface 70 of the PCB 106 and the contact pads 112 may be disposed on the upper surface 68 of the PCB 106. With reference to FIGS. 15A and 15B, the contacts 74 may be disposed on the same side as the contact pads 112. For example, the contacts 74 and the contact pads 112 may be disposed on the upper surface 68.

With reference to FIGS. 14A and 14B, the die 92 and the contacts 74 may be disposed on parallel planes. This allows for a simple, rigid PCB 106 construction. The contacts 74 and the die 92 may be disposed on the same side of the PCB 106 or may be disposed on opposite sides of the PCB 106.

The PCB 106 includes the electrical contacts 74 at the first end and contact pads 112 at the second end proximate the die 92. With reference to FIG. 15A, electrical traces 75 from the contact pads 112 to the electrical contacts are formed on the board and may be covered by the solder mask or another dielectric. Electrical connections from the die 92 to the PCB 106 may be established by a wire bonding process, where small wires, which may be composed of gold or aluminum, are thermally attached to bond pads on the silicon die and to corresponding bond pads on the board. An encapsulant material 116, normally an epoxy compound, is applied to the wire bond area to protect the delicate connections from mechanical damage and other environmental effects.

Figure 13:
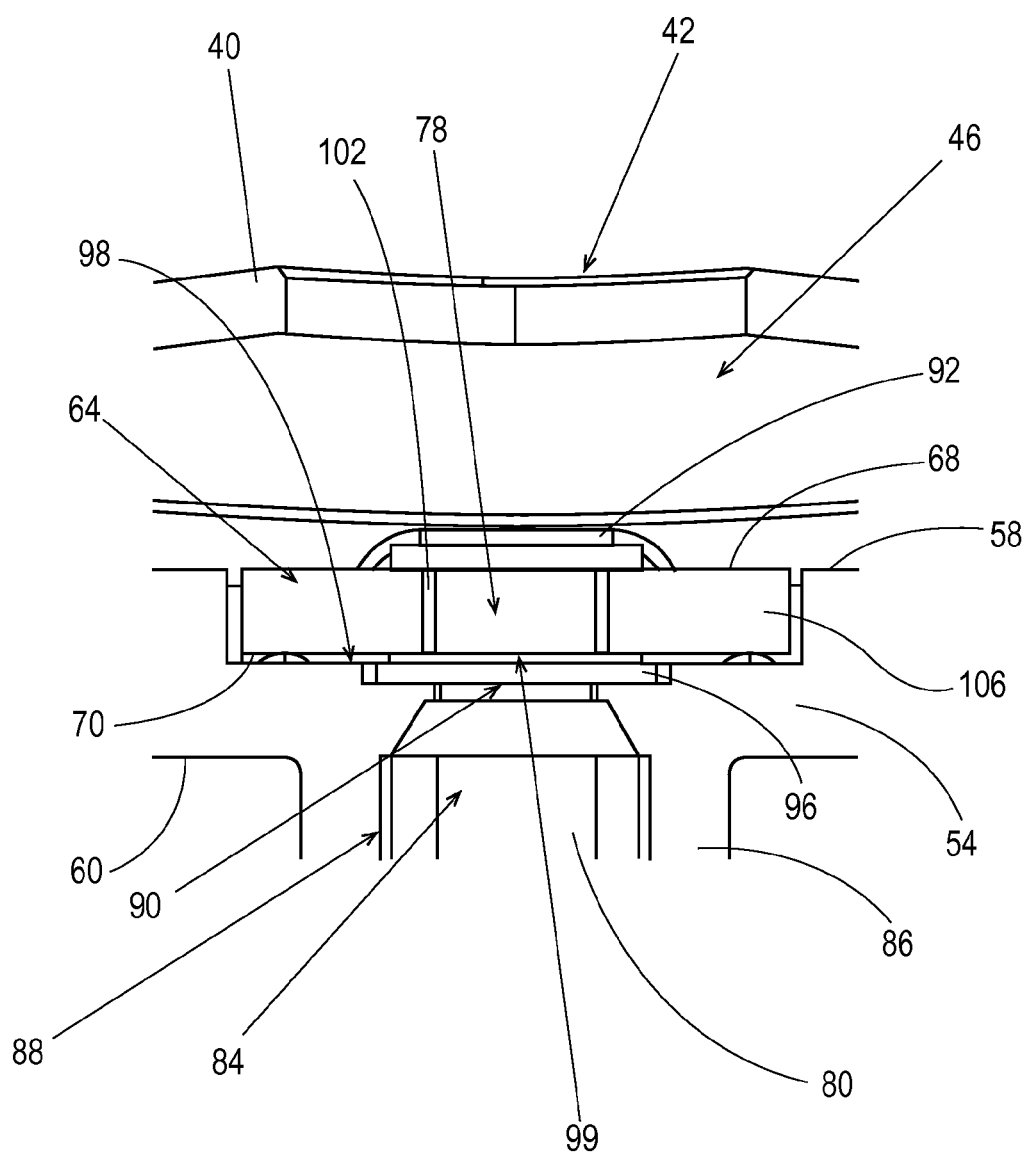
FIG. 13 is an enlarged view of portion 13 of FIG. 7.
Figure 16:
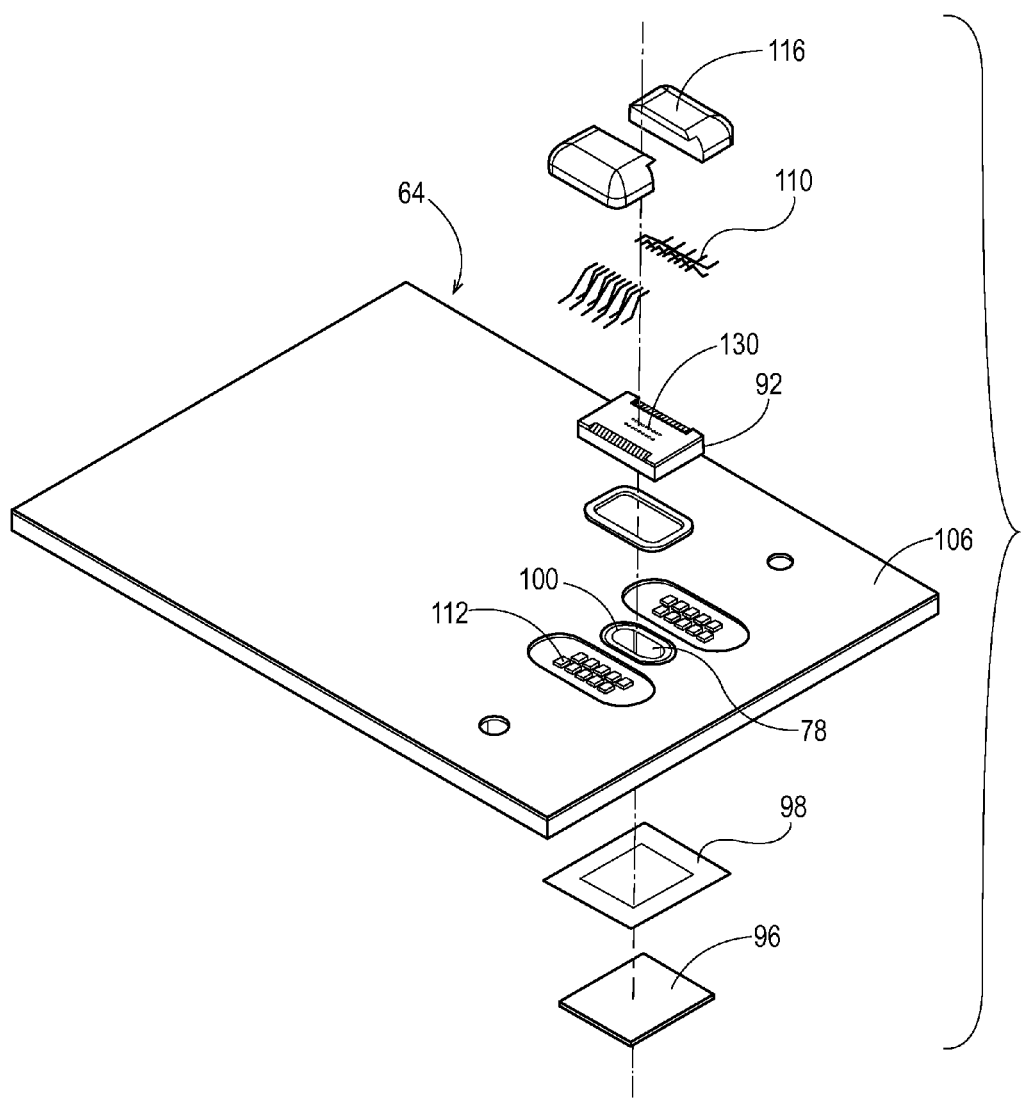
FIG. 16 is an exploded view of a microfluidic delivery member.

With reference to FIGS. 13, 14B, and 16, the microfluidic delivery member 64 may include a filter 96. The filter 96 may be disposed on the lower surface 70 of the PCB 106. The filter 96 may separate the opening 78 of the board from the chamber 88 at the lower surface of the board. The filter 96 may be configured to prevent at least some of particulates from passing through the opening 78 to prevent clogging the nozzles 130 of the die 92. The filter 96 may be configured to block particulates that are greater than one third of the diameter of the nozzles 130. It is to be appreciated that the fluid transport member 80 can act as a suitable filter 96, so that a separate filter is not needed. The filter 96 may be a stainless steel mesh. The filter 96 may be randomly weaved mesh, polypropylene or silicon based.

With reference to FIGS. 13-16, the filter 96 may be attached to the bottom surface with an adhesive material that is not readily degraded by the fluid composition in the reservoir 50. The adhesive may be thermally or ultraviolet activated. The filter 96 is positioned between the chamber 88 and the die 92. The filter 96 is separated from the bottom surface of the microfluidic delivery member 64 by a mechanical spacer 98. The mechanical spacer 98 creates a gap 99 between the bottom surface 70 of the microfluidic delivery member 64 and the filter 96 proximate the opening 78. The mechanical spacer 98 may be a rigid support or an adhesive that conforms to a shape between the filter 96 and the microfluidic delivery member 64. In that regard, the outlet of the filter 96 is greater than the diameter of the opening 78 and is offset therefrom so that a greater surface area of the filter 96 can filter fluid composition than would be provided if the filter was attached directly to the bottom surface 70 of the microfluidic delivery member 64 without the mechanical spacer 98. It is to be appreciated that the mechanical spacer 98 allows suitable flow rates through the filter 96. That is, as the filter 96 accumulates particles, the filter will not slow down the fluid flowing therethrough. The outlet of the filter 96 may be about 4 mm$^2$ or larger and the standoff is about 700 microns thick.

The opening 78 may be formed as an oval, as is illustrated in FIG. 16; however, other shapes are contemplated depending on the application. The oval may have the dimensions of a first diameter of about 1.5 mm and a second diameter of about 700 microns. The opening 78 exposes sidewalls 102 of the PCB 106. If the PCB 106 is an FR4 PCB, the bundles of fibers would be exposed by the opening. These sidewalls are susceptible to fluid composition and thus a liner 100 is included to cover and protect these sidewalls. If fluid composition enters the sidewalls, the PCB 106 could begin to deteriorate, cutting short the life span of this product.

The PCB 106 may carry a die 92. The die 92 comprises a fluid injection system made by using a semiconductor micro fabrication process such as thin-film deposition, passivation, etching, spinning, sputtering, masking, epitaxy growth, wafer/wafer bonding, micro thin-film lamination, curing, dicing, etc. These processes are known in the art to make MEMs devices. The die 92 may be made from silicon, glass, or a mixture thereof. The die 92 comprises a plurality of microfluidic chambers 128, each comprising a corresponding actuation element: heating element or electromechanical actuator. In this way, the die's fluid injection system may be micro thermal nucleation (e.g. heating element) or micro mechanical actuation (e.g. thin-film piezoelectric). One type of die for the microfluidic delivery member is an integrated membrane of nozzles obtained via MEMs technology as described in U.S. 2010/0154790, assigned to STMicroelectronics S.R.I., Geneva, Switzerland. In the case of a thin-film piezo, the piezoelectric material (e.g. lead zirconinum titanate)" is typically applied via spinning and/or sputtering processes. The semiconductor micro fabrication process allows one to simultaneously make one or thousands of MEMS devices in one batch process (a batch process comprises of multiple mask layers).

The die 92 may be secured to the upper surface 68 of the PCB 106 above the opening 78. The die 92 may be secured to the upper surface of the PCB 106 by any adhesive material configured to hold the semiconductor die to the board. The adhesive material may be the same or different from the adhesive material used to secure the filter 96 to the microfluidic delivery member 64.

The die 92 may comprise a silicon substrate, conductive layers, and polymer layers. The silicon substrate forms the supporting structure for the other layers, and contains a channel for delivering fluid composition from the bottom of the die to the upper layers. The conductive layers are deposited on the silicon substrate, forming electrical traces with high conductivity and heaters with lower conductivity. The polymer layers form passages, firing chambers, and nozzles 130 which define the drop formation geometry.

FIGS. 16-20 include more details of the die 92. The die 92 includes a substrate 107, a plurality of intermediate layers 109, and a nozzle plate 132. The nozzle plate 132 includes an outer surface 133 that subtends a surface area. The plurality of intermediate layers 109 include dielectric layers and a chamber layer 148 that are positioned between the substrate and the nozzle plate 132. The nozzle plate 132 may be about 12 microns thick.

The die 92 includes a plurality of electrical connection leads 110 that extend from one of the intermediate layers 109 down to the contact pads 112 on the circuit PCB 106. At least one lead couples to a single contact pad 112. Openings 150 on the left and right side of the die 92 provide access to the intermediate layers 109 to which the leads 110 are coupled. The openings 150 pass through the nozzle plate 132 and chamber layer 148 to expose contact pads 152 that are formed on the intermediate dielectric layers. There may be one opening 150 positioned on only one side of the die 92 such that all of the leads that extend from the die extend from one side while other side remains unencumbered by the leads.

Figure 18:
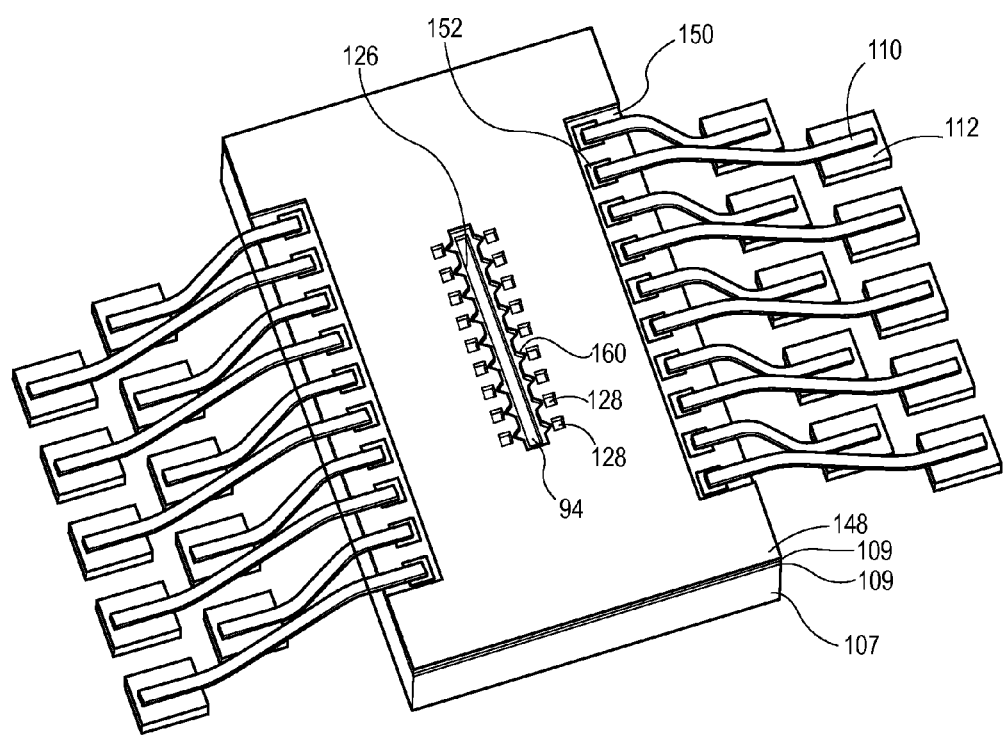
FIG. 18 is a top, perspective view of a die with a nozzle plate removed to show fluid chambers of the die.

The nozzle plate 132 may include about 4-100 nozzles 130, or about 6-80 nozzles, or about 8-64 nozzles. For illustrative purposes only, there are eighteen nozzles 130 shown through the nozzle plate 132, nine nozzles on each side of a center line. Each nozzle 130 may deliver about 0.5 to about 20 picoliters, or about 1 to about 10 picoliters, or about 2 to about 6 picoliters of a fluid composition per electrical firing pulse. The volume of fluid composition delivered from each nozzle per electrical firing pulse may be analyzed using image-based drop analysis where strobe illumination is coordinated in time with the production of drops, one example of which is the JetXpert system, available from ImageXpert, INc. of Nashua, N.H., with the droplets measured at a distance of 1-3 mm from the top of the die. The nozzles 130 may be positioned about 60 um to about 110 μm apart. Twenty nozzles 130 may be present in a 3 mm$^2$ area. The nozzles 130 may have a diameter of about 5 μm to about 40 μm, or 10 μm to about 30 μm, or about 20 μm to about 30 μm, or about 13 μm to about 25 μm. FIG. 18 is a top down isometric view of the die 92 with the nozzle plate 132 removed, such that the chamber layer 148 is exposed.

Figure 20:
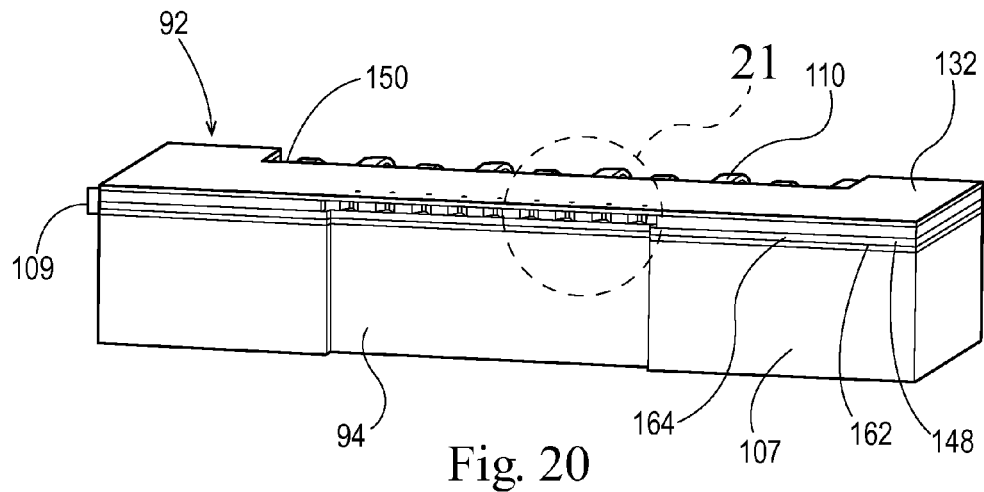
FIG. 20 is a sectional view of FIG. 17 taken along line 20-20.
Figure 21:
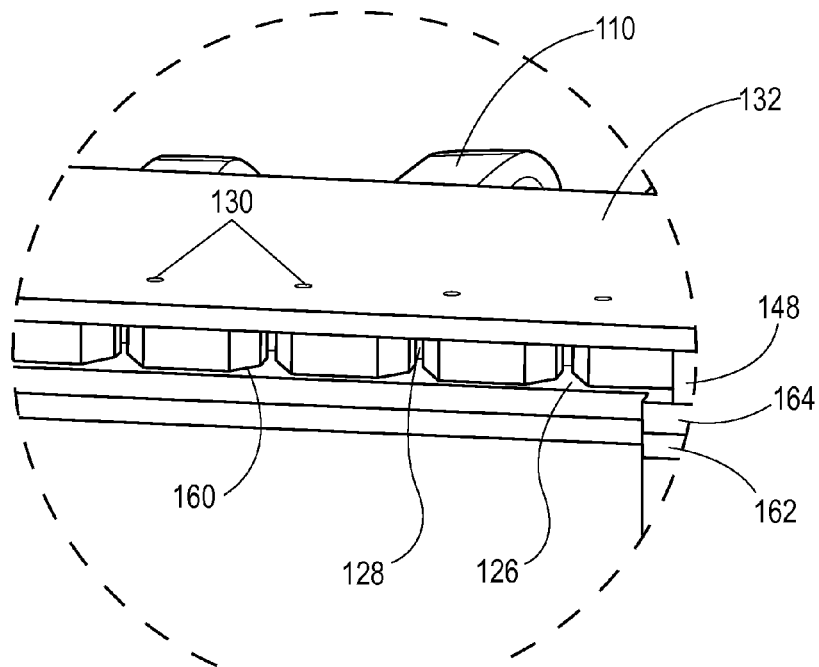
FIG. 21 is an enlarged view of portion 21 taken from FIG. 20.

Generally, the nozzles 130 are positioned along a fluidic feed channel through the die 92 as shown in FIGS. 20 and 21. The nozzles 130 may include tapered sidewalls such that an upper opening is smaller than a lower opening. The heater may be square, having sides with a length. In one example, the upper diameter is about 13 μm to about 18 μm and the lower diameter is about 15 μm to about 20 μm. At 13 μm for the upper diameter and 18 μm for the lower diameter, this would provide an upper area of 132.67 μm and a lower area of 176.63 μm. The ratio of the lower diameter to the upper diameter would be around 1.3 to 1. In addition, the area of the heater to an area of the upper opening would be high, such as greater than 5 to 1 or greater than 14 to 1.

Each nozzle 130 is in fluid communication with the fluid composition in the reservoir 50 by a fluid path. Referring to FIG. 13 and FIGS. 20 and 21, the fluid path from the reservoir 50 includes the first end 82 of the fluid transport member 80, through the transport member to the second end 84 of the transport member, through the chamber 88, through the first through-hole 90, through the opening 78 of the PCB 106, through an inlet 94 of the die 92, then through a channel 126, and then through the chamber 128, and out of the nozzle 130 of the die.

Figure 19:
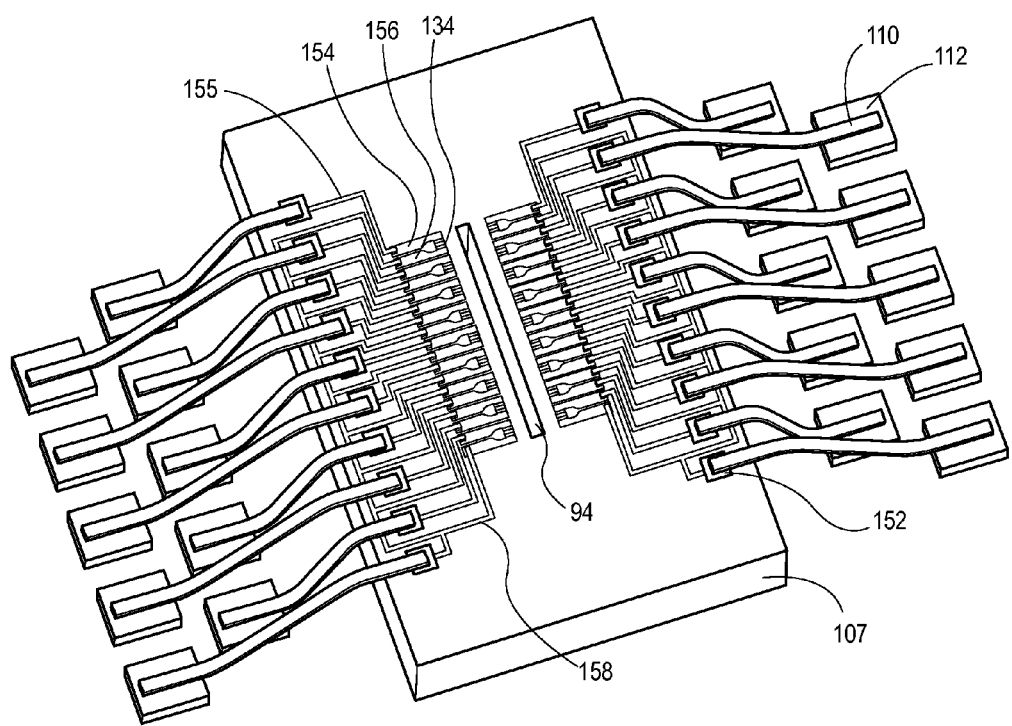
FIG. 19 is a top, perspective view of a die with layers of the die removed to show the dielectric layer of the die.
Figure 22:
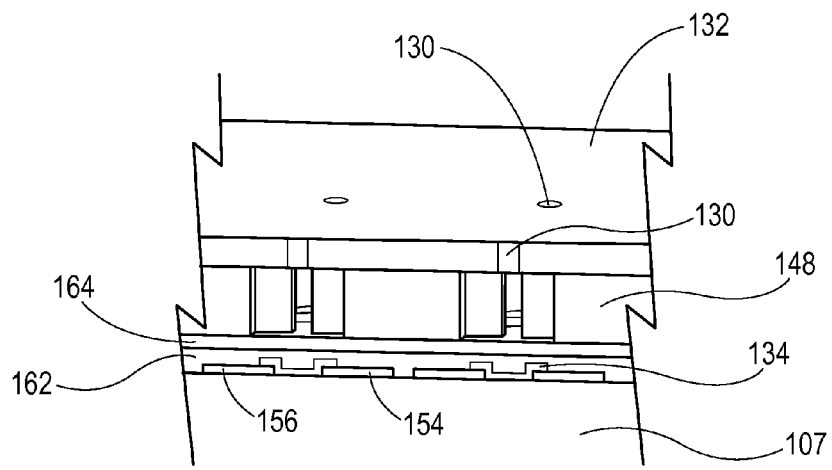
FIG. 22 is a sectional view of FIG. 17 taken along line 22-22.

Proximate each nozzle chamber 128 is a heating element 134 (see FIGS. 19 and 22) that is electrically coupled to and activated by an electrical signal being provided by one of the contact pads 152 of the die 92. Referring to FIG. 19, each heating element 134 is coupled to a first contact 154 and a second contact 156. The first contact 154 is coupled to a respective one of the contact pads 152 on the die by a conductive trace 155. The second contact 156 is coupled to a ground line 158 that is shared with each of the second contacts 156 on one side of the die. There may be only a single ground line that is shared by contacts on both sides of the die. Although FIG. 19 is illustrated as though all of the features are on a single layer, they may be formed on several stacked layers of dielectric and conductive material. Further, while the illustrated embodiment shows a heating element 134 as the activation element, the die 92 may comprise piezoelectric actuators in each chamber 128 to dispense the fluid composition from the die.

In use, when the fluid composition in each of the chambers 128 is heated by the heating element 134, the fluid composition vaporizes to create a bubble. The expansion that creates the bubble causes fluid composition to eject from the nozzle 130 and to form a plume of one or more droplets.

Figure 17:
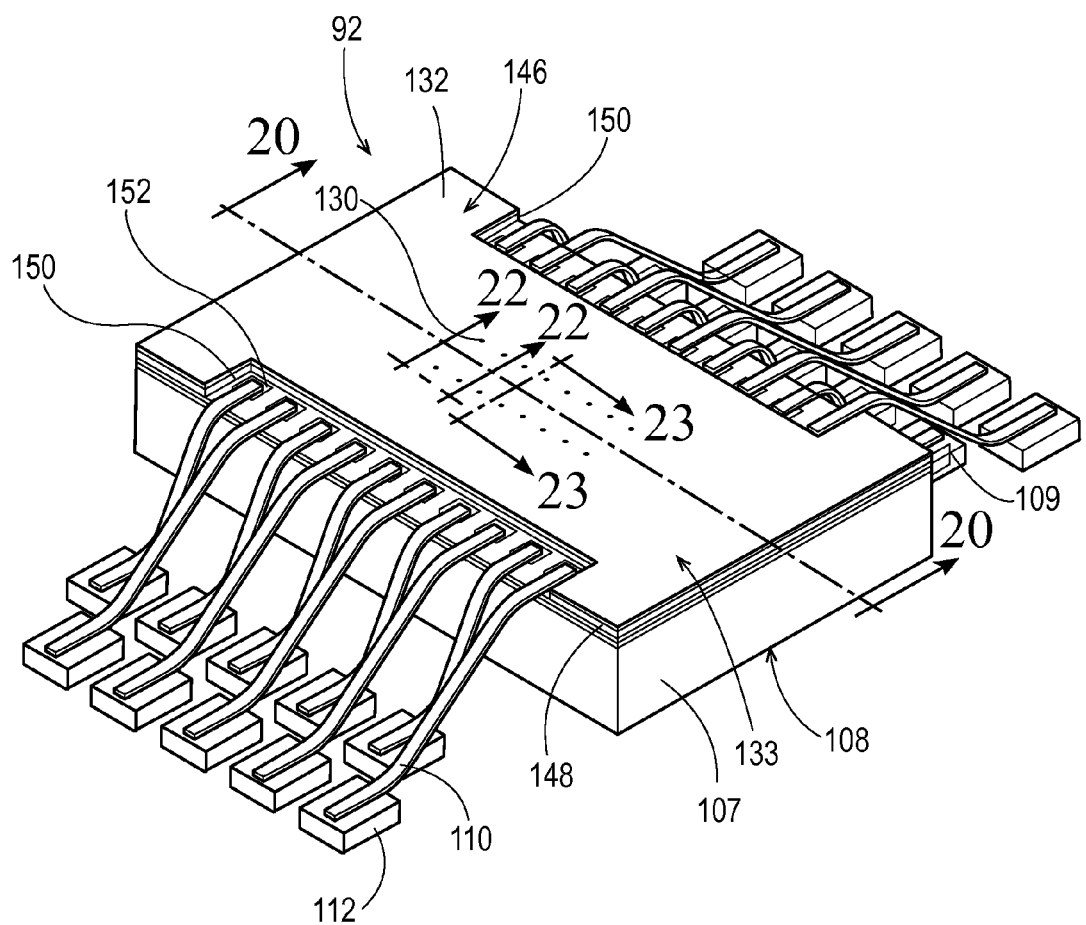
FIG. 17 is a top, perspective view of a die of a microfluidic delivery member.

With reference to FIGS. 17 and 18, the substrate 107 includes an inlet path 94 coupled to a channel 126 that is in fluid communication with individual chambers 128, forming part of the fluid path. Above the chambers 128 is the nozzle plate 132 that includes the plurality of nozzles 130. Each nozzle 130 is above a respective one of the chambers 128. The die 92 may have any number of chambers and nozzles, including one chamber and nozzle. For illustrative purposes only, the die is shown as including eighteen chambers each associated with a respective nozzle. Alternatively, it can have ten nozzles and two chambers provided fluid composition for a group of five nozzles. It is not necessary to have a one-to-one correspondence between the chambers and nozzles.

As best seen in FIG. 18, the chamber layer 148 defines angled funnel paths 160 that feed the fluid composition from the channel 126 into the chamber 128. The chamber layer 148 is positioned on top of the intermediate layers 109. The chamber layer defines the boundaries of the channels and the plurality of chambers 128 associated with each nozzle 130. The chamber layer may be formed separately in a mold and then attached to the substrate. The chamber layer may be formed by depositing, masking, and etching layers on top of the substrate.

The intermediate layers 109 include a first dielectric layer 162 and a second dielectric layer 164. The first and second dielectric layers are between the nozzle plate and the substrate. The first dielectric layer 162 covers the plurality of first and second contacts 154, 156 formed on the substrate and covers the heaters 134 associated with each chamber. The second dielectric layer 164 covers the conductive traces 155.

With reference to FIG. 19, the first and second contacts 154, 156 are formed on the substrate 107. The heaters 134 are formed to overlap with the first and second contacts 154, 156 of a respective heater assembly. The contacts 154, 156 may be formed of a first metal layer or other conductive material. The heaters 134 may be formed of a second metal layer or other conductive material. The heaters 134 are thin-film resistors that laterally connect the first and second contacts 154, 156. Instead of being formed directly on a top surface of the contacts, the heaters 134 may be coupled to the contacts 154, 156 through vias or may be formed below the contacts.

The heater 134 may be a 20-nanometer thick tantalum aluminum layer. The heater 134 may include chromium silicon films, each having different percentages of chromium and silicon and each being 10 nanometers thick. Other materials for the heaters 134 may include tantalum silicon nitride and tungsten silicon nitride. The heaters 134 may also include a 30-nanometer cap of silicon nitride. The heaters 134 may be formed by depositing multiple thin-film layers in succession. A stack of thin-film layers combine the elementary properties of the individual layers.

A ratio of an area of the heater 134 to an area of the nozzle 130 may be greater than seven to one. The heater 134 may be square, with each side having a length 147. The length may be 47 microns, 51 microns, or 71 microns. This would have an area of 2209, 2601, or 5041 microns square, respectively. If the nozzle diameter is 20 microns, an area at the second end would be 314 microns square, giving an approximate ratio of 7 to 1, 8 to 1, or 16 to 1, respectively.

Figure 23:
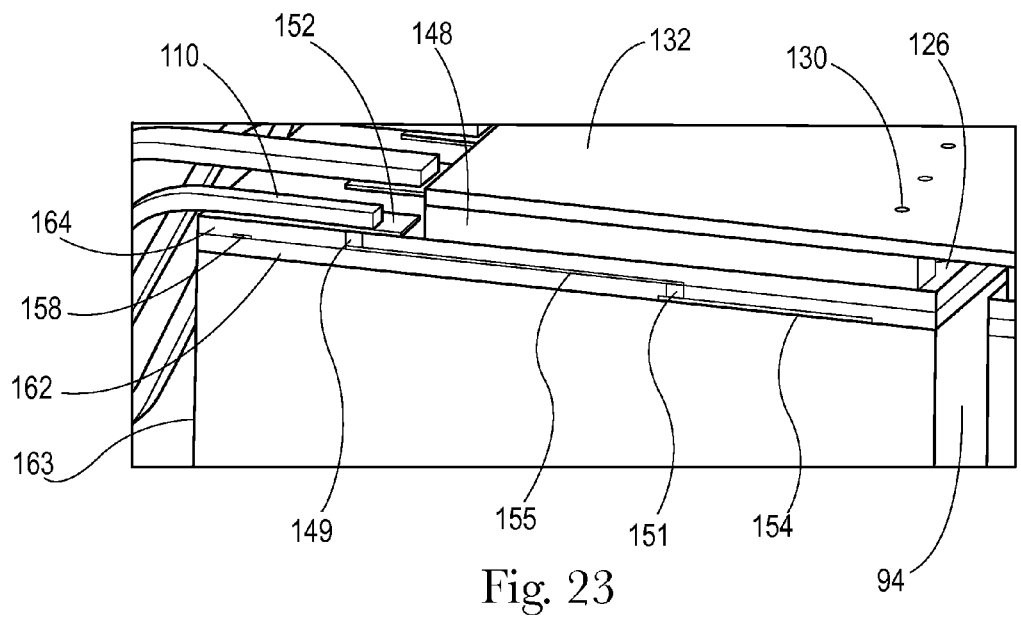
FIG. 23 is a sectional view of FIG. 17 taken along line 23-23.

With reference to FIG. 23, a length of the first contact 154 can be seen adjacent to the inlet 94. A via 151 couples the first contact 154 to trace 155 that is formed on the first dielectric layer 162. The second dielectric layer 164 is on the trace 155. A via 149 is formed through the second dielectric layer 164 and couples the trace 155 to the contact pad 152. A portion of the ground line 158 is visible toward an edge 163 of the die, between the via 149 and the edge 163.

As can be seen in this cross-section, the die 92 may be relatively simple and free of complex integrated circuitry. This die 92 will be controlled and driven by an external microcontroller or microprocessor. The external microcontroller or microprocessor may be provided in the housing. This allows the PCB 106 and the die 92 to be simplified and cost effective. There may be two metal or conductive levels formed on the substrate. These conductive levels include the contact 154 and the trace 155. All of these features can be formed on a single metal level. This allows the die to be simple to manufacture and minimizes the number of layers of dielectric between the heater and the chamber.

Figure 24:
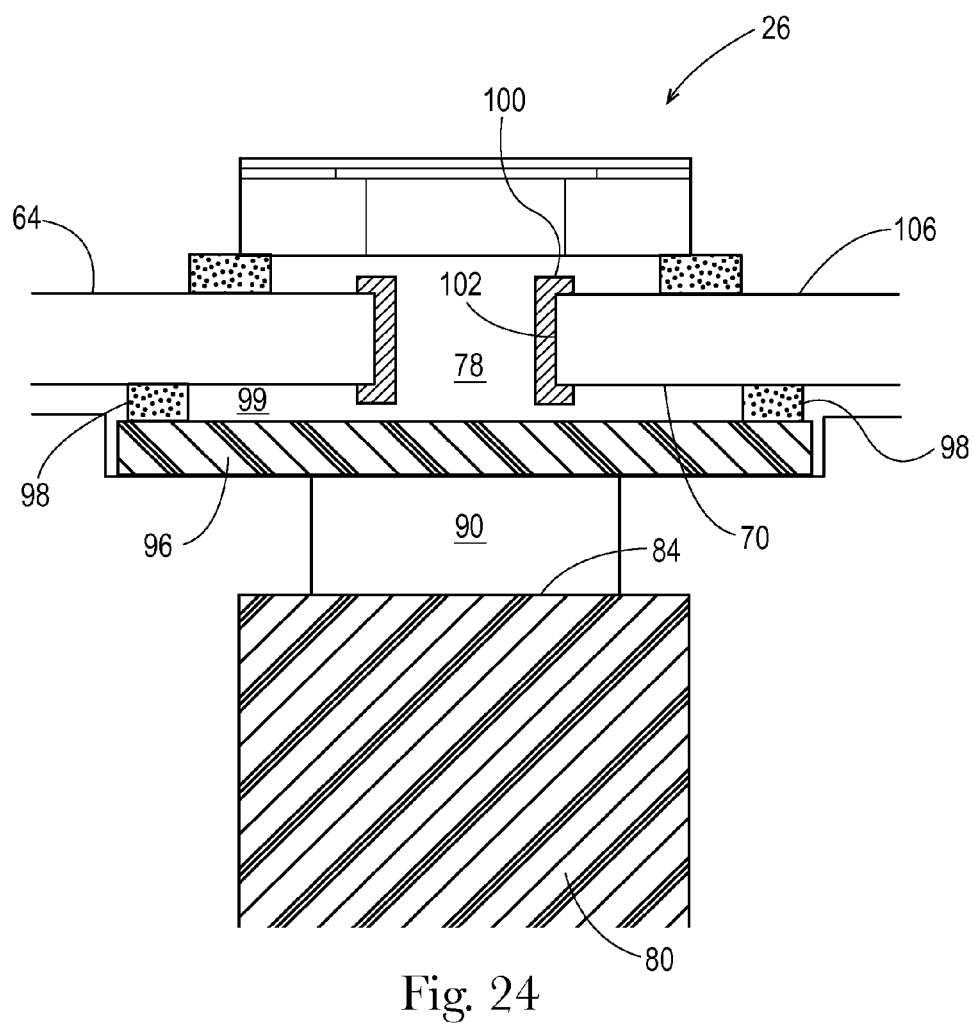
FIG. 24 is a sectional view of a portion of a fluid path of a microfluidic delivery member.

Referring now to FIG. 24, there is provided a close-up view of a portion of a microfluidic cartridge 26 illustrating a flow path with a filter 96 between the second end 84 of the fluid transport member 80 and the die 92. The opening 78 of the microfluidic delivery member 64 may include a liner 100 that covers exposed sidewalls 102 of the PCB 106. The liner 100 may be any material configured to protect the PCB 106 from degradation due to the presence of the fluid composition, such as to prevent fibers of the board from separating. In that regard, the liner 100 may protect against particles from the PCB 106 entering into the fluid path and blocking the nozzles 130. For instance, the opening 78 may be lined with a material that is less reactive to the fluid composition in the reservoir than the material of the PCB 106. In that regard, the PCB 106 may be protected as the fluid composition passes therethrough. The through hole may be coated with a metal material, such as gold.

Outer Cover

With reference to FIGS. 6-10, the cartridge 26 includes an outer cover 40. The outer cover 40 may be defined by an interior 49 and an exterior 63. The outer cover 40 may include a top 41 that is defined by a perimeter 43. The top 41 of the outer cover 40 may be defined by a surface area that is bounded by the perimeter 43. The top 41 includes an orifice 42. The top 41 of the outer cover 40 may substantially cover the top portion 51 of the reservoir 50. The orifice 42 may be disposed adjacent to the die 92. The orifice 42 may be at least partially aligned with the die 92. The orifice 42 may expose the die 92 to the exterior 23 of the housing 12.

The outer cover 40 is connected with the reservoir 50 such that a gap is formed between the outer cover 40 and the reservoir 50, forming an air flow path 46 between the outer cover 40 and the reservoir 50. The air flow path 46 allows air from the fan 32 to force the fluid composition 52 dispensed from the microfluidic delivery member 64 out of the orifice 42 and into the room or space. Restricting the air flow and the dispensed fluid composition 52 to flow through the orifice 42 can increase the velocity of the fluid composition 52 dispensed from the cartridge 26. Generally, the greater the velocity of the fluid composition 52 dispensed from the cartridge 26, the greater the distance the fluid composition 52 will be able to travel into the air; thus, the velocity of the fluid composition 52 can positively impact the dispersion of the fluid composition 52 into a room or space. The size of the orifice 42 can directly impact the velocity of the fluid composition 52 due to the air velocity of the air from the fan.

The outer cover 40 may include a skirt 45 that extends from the perimeter 43 of the top 41 toward the reservoir 50. The skirt 45 may surround at least a portion of the sidewall(s) 61 of the reservoir 50. The skirt 45 may be configured such that air is able to flow longitudinally adjacent to the sidewall(s) 61 of the reservoir 50. Air may flow longitudinally through the air flow path. Moreover, directing the air flow from the fan 32 through the air flow path 46 allows for a uniform flow of air from the skirt 45 to the orifice 42, minimizing the opportunity for turbulence to form inside of the outer cover 40 that could cause dispensed fluid composition 52 to become trapped in the air flow path 46 and possibly redeposited onto the die 92.

The outer cover 40, including the top 41 and/or the skirt 45, may cover at least a portion of the microfluidic delivery member 64. The outer cover 40 may cover the entire microfluidic delivery member 64. With reference to FIGS. 8 and 9, with a semi-flex PCB 106, the top 41 of the outer cover 40 may cover a portion of the PCB 106 and the skirt 45 may cover a portion of the PCB 106 because the PCB 106 extends from the top portion 51 to the sidewall(s) 61 of the reservoir 50. With reference to FIG. 10, in a cartridge comprising a rigid PCB 106, the top 41 of the outer cover 40 may cover substantially all of the PCB 106. In such an exemplary configuration, the outer cover 40 may or may not include a skirt 45. Covering the electrical contacts 74 and the die 92 of the microfluidic delivery member 64 can prevent damage that may be caused by a user touching the electrical contacts 74 and/or die 92. For example, oil and/or dirt on a user's hands can clog the die 92 and prevent fluid composition from releasing through the nozzles 130 of the die 92. Also, oil and/or dirt on a user's hands can damage the electrical contacts 74 can decrease the strength of the electrical connection between the electrical contacts 74 on the microfluidic delivery member 64 and the electrical contacts 48 on the housing 12.

Moreover, the skirt 45 of the outer cover 40 provides a safe and/or ergonomic surface for a user to grasp as the user inserts and removes the cartridge 26 from the housing 12 without damaging the microfluidic delivery member 64. The outer cover 40 can also improve the aesthetic appearance of the cartridge 26 by covering the microfluidic delivery member 64.

The orifice 42 may expose at least a portion of, or substantially all of, or all of, the die 92. By exposing at least a portion of the die 92, the fluid composition dispensed from the die 92 is unrestricted as it passes through the orifice 42. As a result, deposition of fluid composition onto the outer cover 40 after it is dispensed from the die 92 may be kept to a minimum or even prevented.

The outer cover 40 may be configured such that air flow through the air flow path 46 increases in pressure from the skirt 45 to the orifice 42. The air flow path 46 may continually increase in pressure from the skirt 4*t* to the orifice 432. It is to be appreciated that if the pressure through the air flow path 46 is increased and then decreased before the air exits the orifice 42, eddies may be formed that reduce the air flow out of the orifice 42 or cause fluid composition 52 to become trapped in the air flow path 46 or on the top portion 51 of the reservoir 50.

The orifice 42 may be defined by a perimeter 65 and a surface area that is bounded by the perimeter 65 of the orifice 42. The surface area of the orifice 42 may be greater than the surface area of the nozzle plate 132. The surface area of the orifice 42 may be at least 10%, or at least 20%, or at least 30% greater than the surface area of the nozzle plate 132. The orifice 42 may have a surface area of about 40 $mm^2$ to about 200 $mm^2$, or about 75 $mm^2$ to about 150 $mm^2$. The surface area of the orifice 42 may be at least 5%, or at least 10%, or at least 15%, or at least 20% of the surface area of the top 41. It is to be appreciated that the surface area of the orifice 42 can impact the velocity of fluid composition and air flow exiting the orifice 42; a smaller surface area of the orifice may result in a lower velocity of air flow and fluid composition exiting the orifice 42.

The perimeter 65 of the orifice 42 may be configured in various different shapes. For example, the orifice 42 may have a circular, arcuate, square, rectangular, star, polygon, or various other shapes. The orifice 42 may be concentric or eccentric with the top 41 of the outer cover 40. The orifice 42 may be congruent with the top 41 of the outer cover 42.

The outer cover 40 may be connected with the reservoir 50 in various ways, including permanently or releasably. For example, the outer cover 40 may be welded, glued, friction-fitted, or the like, to the reservoir 50. One or more connection elements 47 of the outer cover 40 may mate with one or more connection elements 62 on the reservoir 50, or one or more connection elements 47 of the outer cover 40 may mate with the reservoir 50. The connection elements 47 on the outer cover may be welded or glued to the connection elements 62 on the reservoir 50 to permanently fix the outer cover 40 to the reservoir 50. Permanently or temporarily fixing the outer cover 40 to the reservoir 50 prevents the outer cover 40 from moving relative to the reservoir 50 as air from the fan 32 flows through the air flow path 46 between the outer cover 40 and the reservoir 46. The location of the connection elements 47 on the outer cover 40 may be the only location where a gap does not exist between the outer cover 40 and the reservoir 50. As such, the connection elements 47 on the outer cover 47 and the connection elements 62 on the reservoir 50 may be relatively small in order to allow the air to flow toward the orifice 42 of the outer cover 40.

The outer cover 40 may have various shapes. For example, the top 41 of the outer cover 40 may be flat, substantially flat, curved, waved, or the like. The shape of the top 41 of the outer cover 40 may be symmetrical, asymmetrical, regular, or irregular. The exterior 63 of the outer cover 40 may have various textures, including smooth, bumpy, wavy, or the like. The top 41 of the outer cover 40 may have the same surface texture as the skirt 45 of the outer cover 40, or may have a different surface texture than the skirt 45. The skirt 45 of the outer cover 40 may have a texture or indentation(s) for a user to grip as the user is inserting or removing the cartridge 26 from the housing 10.

The outer cover 40 may have various dimensions. For example, the skirt 45 of the outer cover 40 may be defined by a length L extending from the perimeter 43 of the top 41 of the outer cover 40 that extends down toward the base portion 53 of the reservoir 50. For example, the length L may be in the range of about 5 millimeters to about 25 millimeters, or about 10 millimeters to about 20 millimeters. The skirt 45 of the outer cover 40 may cover a portion of the sidewall(s) 61 of the reservoir 50. For example, the skirt 45 of the outer cover 40 may cover at least 10% or at least 20% or at least 30% of the surface area of the sidewall(s) 61 of the reservoir 50. The outer cover 40 may be appropriately sized in order to form the desired air flow path 46 dimensions formed in the gap between the outer cover 40 and the reservoir 50. The thickness of the outer cover 40, including the skirt 45 and the top 41, may have various dimensions, depending upon the desired strength and durability and on the material of the outer cover 40. The thickness of the outer cover 40 may be uniform or non-uniform.

Figure 11:
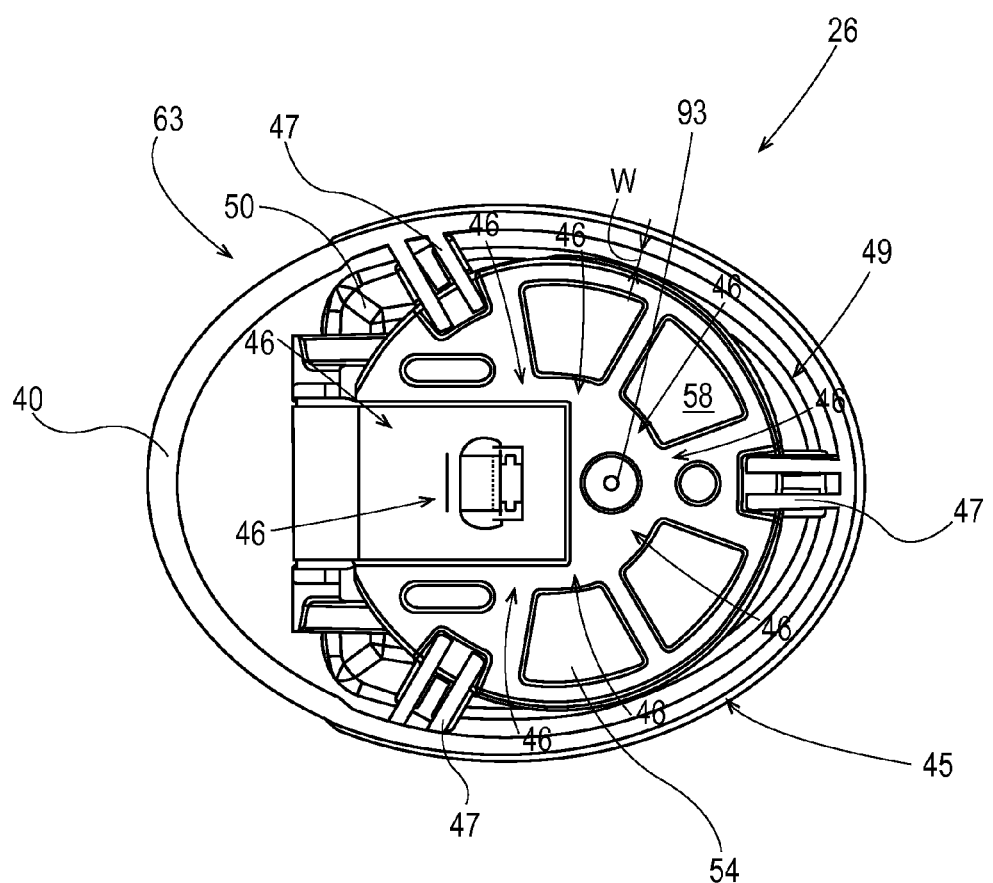
FIG. 11 is a sectional view of FIG. 6 taken along line 11-11.
Figure 12:
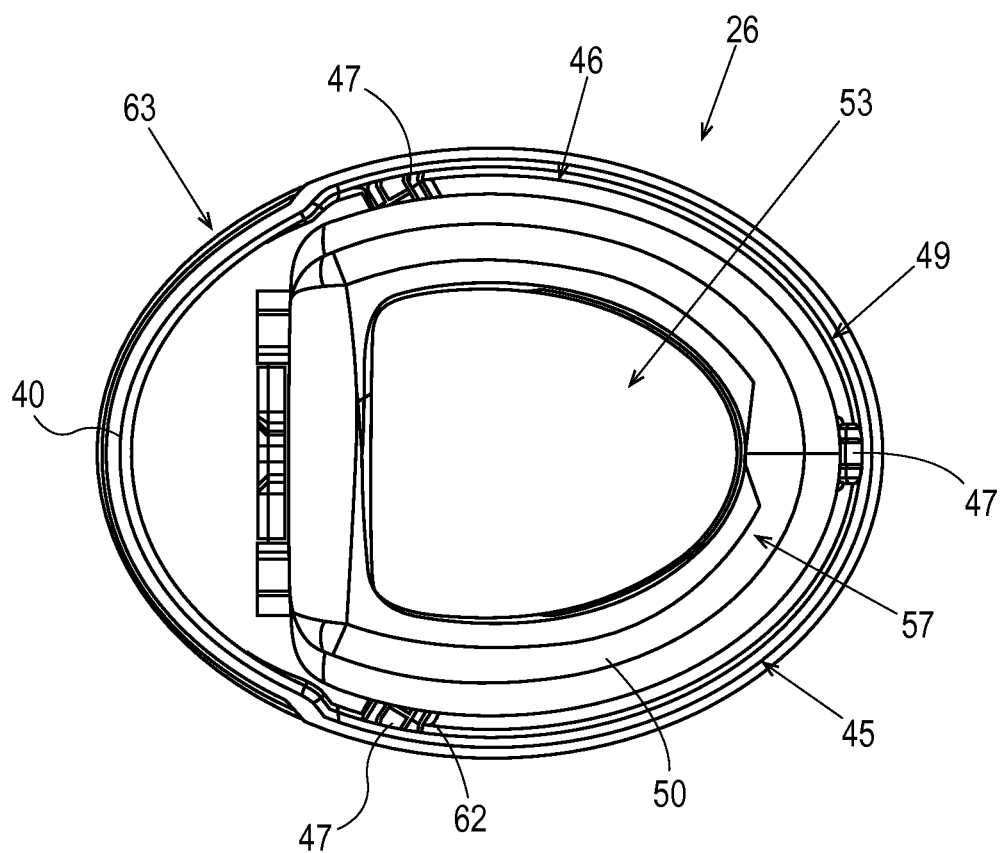
FIG. 12 is a bottom, plan view of the cartridge of FIG. 6

With reference to FIG. 11, the air flow path 46 may be defined by a width W extending between the reservoir 50 and the outer cover 40. The width W may be at least 2 millimeters, or at least 2.5 millimeters, or at least 3 millimeters. The width W of the air flow path 46 may be in the range of about 2 millimeters to about 5 millimeters. The width W of the air flow path 46 may be uniform or may vary because of the non-uniform surface and various structural components of the reservoir 50 and/or the outer cover 40.

The outer cover 40 may be comprised of various materials. For example, the outer cover 40 may be comprised of a rigid polymeric material, such as Copolyester TRITAN® from Eastman, Polypropylene, Nylon, PBT, or other perfume or solvent resistant plastics. The outer cover 40 may be the same material as the reservoir 50 or a different material than the reservoir 50. The outer cover 40 may be the same color as the reservoir 50 or may be a different color than the reservoir 50. The outer cover 40 may be transparent or opaque so that the microfluidic delivery member 64 is less visible or not visible from the exterior 63 of the outer cover 40.

In a configuration having a lid 54 form a portion of the reservoir 50, the outer cover 40 may surround at least a portion of the lid 54. The outer cover 40 may cover the entire lid 54.

The outer cover 40 may include a screen that overlaps with the orifice 42 of the outer cover 40. The screen may prevent a user from accessing the microfluidic delivery member 64.

Sensors

The delivery system may include commercially available sensors that respond to environmental stimuli such as light, noise, motion, and/or odor levels in the air. For example, the delivery system can be programmed to turn on when it senses light, and/or to turn off when it senses no light. In another example, the delivery system can turn on when the sensor senses a person moving into the vicinity of the sensor. Sensors may also be used to monitor the odor levels in the air. The odor sensor can be used to turn-on the delivery system, increase the heat or fan speed, and/or step-up the delivery of the fluid composition from the delivery system when it is needed.

VOC sensors can be used to measure intensity of perfume from adjacent or remote devices and alter the operational conditions to work synergistically with other perfume devices. For example a remote sensor could detect distance from the emitting device as well as fragrance intensity and then provide feedback to device on where to locate device to maximize room fill and/or provide the "desired" intensity in the room for the user.

The devices may communicate with each other and coordinate operations in order to work synergistically with other perfume devices.

The sensor may also be used to measure fluid composition levels in the reservoir or count firing of the heating elements to indicate the cartridge's end-of-life in advance of depletion. In such case, an LED light may turn on to indicate the reservoir needs to be filled or replaced with a new reservoir.

The sensors may be integral with the delivery system housing or in a remote location (i.e. physically separated from the delivery system housing) such as remote computer or mobile smart device/phone. The sensors may communicate with the delivery system remotely via low energy blue tooth, 6 low pan radios or any other means of wirelessly communicating with a device and/or a controller (e.g. smart phone or computer).

The user may be able to change the operational condition of the device remotely via low energy blue tooth, or other means.

Smart Chip

The cartridge 26 may include a memory in order to transmit optimal operational condition to the device.

Fluid Composition

To operate satisfactorily in a microfluidic delivery system, many characteristics of a fluid composition are taken into consideration. Some factors include formulating fluid compositions with viscosities that are optimal to emit from the microfluidic delivery member, formulating fluid compositions with limited amounts or no suspended solids that would clog the microfluidic delivery member, formulating fluid compositions to be sufficiently stable to not dry and clog the microfluidic delivery member, etc. Operating satisfactorily in a microfluidic delivery system, however, addresses only some of the requirements necessary for a fluid composition having more than 50 wt. % of a perfume mixture to atomize properly from a microfluidic delivery member and to be delivered effectively as an air freshening or malodor reducing composition.

The fluid composition may exhibit a viscosity of less than 20 centipoise ("cps"), alternatively less than 18 cps, alternatively less than 16 cps, alternatively from about 5 cps to about 16 cps, alternatively about 8 cps to about 15 cps. And, the volatile composition may have surface tensions below about 35, alternatively from about 20 to about 30 dynes per centimeter. Viscosity is in cps, as determined using the Bohlin CVO Rheometer system in conjunction with a high sensitivity double gap geometry.

The fluid composition is free of suspended solids or solid particles existing in a mixture wherein particulate matter is dispersed within a liquid matrix. Free of suspended solids is distinguishable from dissolved solids that are characteristic of some perfume materials.

The fluid composition may comprise volatile materials. Exemplary volatile materials include perfume materials, volatile dyes, materials that function as insecticides, essential oils or materials that acts to condition, modify, or otherwise modify the environment (e.g. to assist with sleep, wake, respiratory health, and like conditions), deodorants or malodor control compositions (e.g. odor neutralizing materials such as reactive aldehydes (as disclosed in U.S. 2005/0124512), odor blocking materials, odor masking materials, or sensory modifying materials such as ionones (also disclosed in U.S. 2005/0124512)).

The volatile materials may be present in an amount greater than about 50%, alternatively greater than about 60%, alternatively greater than about 70%, alternatively greater than about 75%, alternatively greater than about 80%, alternatively from about 50% to about 100%, alternatively from about 60% to about 100%, alternatively from about 70% to about 100%, alternatively from about 80% to about 100%, alternatively from about 90% to about 100%, by weight of the fluid composition.

The fluid composition may contain one or more volatile materials selected by the material's boiling point ("B.P."). The B.P. referred to herein is measured under normal standard pressure of 760 mm Hg. The B.P. of many perfume ingredients, at standard 760 mm Hg can be found in "Perfume and Flavor Chemicals (Aroma Chemicals)," written and published by Steffen Arctander, 1969.

The fluid composition may include a perfume mixture of one or more perfume materials. The perfume mixture may have an average boiling point of less than 275° C., alternatively less than 250° C., alternatively less than 220° C., alternatively less than about 180° C., alternatively about 70° C. to about 250° C. A quantity of low B.P. ingredients (<200° C.) in the perfume mixture can be used to help higher boiling point formulations to be ejected. A fluid composition with a boiling point above 250° C. could be made to eject with good performance if the fluid composition comprises from about 50% to about 100%, or about 60% to about 100%, or about 75% to about 100%, by weight of the fluid composition, of a perfume mixture of volatile perfume materials, wherein the perfume mixture has an average boiling point of less than 250° C., or less than 225° C. despite the overall average of the fluid composition still being above 250° C.

The fluid composition may comprise, consist essentially of, or consist of volatile perfume materials.

Tables 2 and 3 outline technical data on perfume materials suitable for the present fluid composition 52. Approximately 10%, by weight of the fluid composition, may be ethanol, which may be used as a diluent to reduce boiling point to a level less than 250° C. Flash point may be considered in choosing the perfume formulation as flash points less than 70° C. require special shipping and handling in some countries due to flammability. Hence, there may be advantages to formulate to higher flash points.

Table 2 lists some non-limiting, exemplary individual perfume materials suitable for the present fluid composition.

TABLE 2

| CAS Number | Perfume Raw Material Name | B.P. (° C.) |
|---|---|---|
| 105-37-3 | Ethyl propionate | 99 |
| 110-19-0 | Isobutyl acetate | 116 |
| 928-96-1 | Beta gamma hexenol | 157 |
| 80-56-8 | Alpha Pinene | 157 |
| 127-91-3 | Beta Pinene | 166 |
| 1708-82-3 | cis-hexenyl acetate | 169 |
| 124-13-0 | Octanal | 170 |
| 470-82-6 | Eucalyptol | 175 |
| 141-78-6 | Ethyl acetate | 77 |

Table 3 shows an exemplary perfume mixture having a total B.P. less than 200° C.

TABLE 3

| CAS Number | Perfume Raw Material Name | Wt % | B.P. (° C.) |
|---|---|---|---|
| 123-68-2 | Allyl Caproate | 2.50 | 185 |
| 140-11-4 | Benzyl Acetate | 3.00 | 214 |
| 928-96-1 | Beta Gamma Hexenol | 9.00 | 157 |
| 18479-58-8 | Dihydro Myrcenol | 5.00 | 198 |
| 39255-32-8 | Ethyl 2 Methyl Pentanoate | 9.00 | 157 |
| 77-83-8 | Ethyl Methyl Phenyl Glycidate | 2.00 | 260 |
| 7452-79-1 | Ethyl-2-Methyl Butyrate | 8.00 | 132 |
| 142-92-7 | Hexyl Acetate | 12.50 | 146 |
| 68514-75-0 | Orange Phase Oil 25X1.18%-Low Cit. 14638 | 10.00 | 177 |
| 93-58-3 | Methyl Benzoate | 0.50 | 200 |
| 104-93-8 | Para Cresyl Methyl Ether | 0.20 | 176 |
| 1191-16-8 | Prenyl Acetate | 8.00 | 145 |
| 88-41-5 | Verdox | 3.00 | 223 |
| 58430-94-7 | Iso Nonyl Acetate | 27.30 | 225 |
| | TOTAL: | 100.00 | |

The fluid composition may also include solvents, diluents, extenders, fixatives, thickeners, or the like. Non-limiting examples of these materials are ethyl alcohol, carbitol, diethylene glycol, dipropylene glycol, diethyl phthalate, triethyl citrate, isopropyl myristate, ethyl cellulose, and benzyl benzoate.

The fluid composition may contain functional perfume components ("FPCs"). FPCs are a class of perfume raw materials with evaporation properties that are similar to traditional organic solvents or volatile organic compounds ("VOCs"). "VOCs", as used herein, means volatile organic compounds that have a vapor pressure of greater than 0.2 mm Hg measured at 20° C. and aid in perfume evaporation. Exemplary VOCs include the following organic solvents: dipropylene glycol methyl ether ("DPM"), 3-methoxy-3-methyl-1-butanol ("MMB"), volatile silicone oil, and dipropylene glycol esters of methyl, ethyl, propyl, butyl, ethylene glycol methyl ether, ethylene glycol ethyl ether, diethylene glycol methyl ether, diethylene glycol ethyl ether, or any VOC under the tradename of Dowanol™ glycol ether. VOCs are commonly used at levels greater than 20% in a fluid composition to aid in perfume evaporation.

The FPCs of the present fluid composition aid in the evaporation of perfume materials and may provide a hedonic, fragrance benefit. FPCs may be used in relatively large concentrations without negatively impacting perfume character of the overall composition. As such, The fluid composition may be substantially free of VOCs, meaning it has no more than 18%, alternatively no more than 6%, alternatively no more than 5%, alternatively no more than 1%, alternatively no more than 0.5%, by weight of the composition, of VOCs. The volatile composition may be free of VOCs.

Perfume materials that are suitable as FPCs are disclosed in U.S. Pat. No. 8,338,346.

Method of Operation

With reference to FIGS. 2-4 and 6-8, the microfluidic delivery system 10 may deliver a fluid composition 52 from the cartridge 26 using thermal heating or vibration via piezoelectric crystals, for example. The fluid transport member 80 directs fluid composition 52 contained within the reservoir 50 toward the die 92 of the microfluidic delivery member 64. The fluid transport member 80 may be configured to direct the fluid composition 52 up, opposite the force of gravity to the die 92. After passing through the second end portion 84 of the fluid transport member 80, the fluid composition 52 travels through the die 92.

In a microfluidic delivery system that utilizes thermal inkjet technology, the fluid composition 52 travels through the fluid channel 156 and into the inlet 184 of each fluid chamber 180. The fluid composition 52, which may comprise in part a volatile component, travels through each fluid chamber 128 to the heater 134 of each fluid chamber 128. The heater 134 vaporizes at least a portion of the volatile components in the fluid composition 52, causing a vapor bubble form. The expansion created by the vapor bubble causes a droplet of fluid composition 52 to be ejected through the nozzle 130. The vapor bubble then collapses and causes the droplet of fluid composition 52 to break away and release from the orifice 130. The fluid composition 52 then refills the fluid chamber 128 and the process may be repeated to atomize additional droplets of fluid composition 52.

The fan 32 pulls air from the air inlet(s) 27 into the interior 21 of the housing in order to pressurize the air in the interior 21 of the housing 12. Because fluid will travel from an area of high pressure to an area of low pressure, the air in the interior 21 of the housing 12 will follow the least restrictive path to reach the exterior 23 of the housing 12. As a result, the housing 12 may be configured such that the pressurized air in the interior 21 of the housing 12 flows through the air flow channel 34 between the holder 24 and the upper portion 14 of the housing 12. From the air flow channel 34, the pressurized air will flow through the air flow path 46 between the outer cover 40 and the reservoir 50. If the outer cover 40 of the cartridge 26 is not sealably engaged with the housing 12, some air may escape through the gap between the outer cover 40 and the housing 12. The air flow through the gap between the outer cover 40 and the housing 12 may be reduced by configuring the flow path through the air flow channel 34 and the air flow path 46 to be the path of least resistance to the exterior 23 of the housing 12.

The air flowing through the air flow path 46 combines with the fluid composition 52 that was atomized from the microfluidic delivery member 64. Then, the combined fluid composition 52 and air flow exit out of the orifice 42 of the outer cover 40. The shape of the air flow path 46 may direct the air out of the orifice 42 in the same or substantially the same direction as the direction the fluid composition 52 is being dispensed from the die 92. The air provides additional force, in addition to the force of dispensing the atomized fluid composition 52 from the microfluidic delivery member 64, to direct the fluid composition 52 into the air.

Other ejection processes may be used in addition or in the alternative to heaters used to atomize the fluid composition 52. For instance, piezoelectric crystal elements or ultrasonic fluid ejection elements may be used to atomize the fluid composition from the die 92.

The output of the microfluidic delivery system 10 may be adjustable or programmable. For example, the timing between releases of droplets of fluid composition 52 from the microfluidic delivery system 10 may be any desired timing and can be predetermined or adjustable. Further, the flow rate of fluid composition released from the microfluidic delivery system 10 can be predetermined or adjustable. For example, the microfluidic delivery system 10 may be configured to deliver a predetermined amount of the fluid composition 52, such as a perfume, based on a room size or may be configured to be adjustable as desired by the user. For exemplary purposes only, the flow rate of fluid composition 52 released from the cartridge 26 could be in the range of about 5 to about 60 mg/hour or any other suitable rate or range.

The microfluidic delivery system 10 may be used to deliver a fluid composition into the air. The microfluidic delivery system 10 may also be used to deliver a fluid composition onto a surface.

Upon depletion of the fluid composition in the reservoir 50, the microfluidic cartridge 26 may be removed from the housing 10 and replaced with another microfluidic cartridge 26.

All percentages stated herein are by weight unless otherwise specified.

Values disclosed herein as ends of ranges are not to be understood as being strictly limited to the exact numerical values recited. Instead, unless otherwise specified, each numerical range is intended to mean both the recited values, any integers within the specified range, and any ranges with the specified range. For example a range disclosed as “1 to 10” is intended to mean “1, 2, 3, 4, 5, 6, 7, 8, 9, 10.”

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as “40 mm” is intended to mean “about 40 mm.”

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cartridge for a microfluidic delivery system, the cartridge having a longitudinal axis and comprising:
    a reservoir for containing a fluid composition;
    a nozzle operatively connected with the reservoir, wherein the nozzle is in fluid communication with the reservoir for releasing the fluid composition;
    an outer cover operatively connected with the reservoir, the outer cover comprising an orifice that is adjacent to the nozzle, wherein an air flow path is formed by a gap between the reservoir and the outer cover.

2. The cartridge of claim 1, wherein the reservoir comprises a top portion, a base portion opposing the top portion, and at least one sidewall extending between and connecting the top and base portions, wherein the outer cover comprises a top and a skirt extending from the top, wherein the top comprises the orifice of the outer cover, and wherein the gap is disposed between the skirt and the sidewall of the reservoir, and wherein at least a portion of the air flow path between the skirt and the sidewall extends longitudinally.

3. The cartridge of claim 1, wherein the orifice and the nozzle are at least partially longitudinally aligned.

4. The cartridge of claim 1 further comprising a die in fluid communication with the reservoir, wherein the die comprises the nozzle.

5. The cartridge of claim 4, wherein the die comprises a heater.

6. The cartridge of claim 4, wherein the die comprises a piezoelectric crystal.

7. The cartridge of claim 4, wherein the die comprises nozzle plate, wherein the orifice is defined by a surface area, wherein the surface area of the orifice is larger than the nozzle plate.

8. The cartridge of claim 1, wherein fluid composition dispensed from the nozzle combines with air traveling through the air flow path, wherein the combined fluid composition and air exit the cartridge at the orifice.

9. The cartridge of claim 1, wherein the air flow path is defined by a width extending between the outer cover and the reservoir, wherein the width is at least 2 millimeters.

10. A cartridge for a microfluidic delivery system, the cartridge having a longitudinal axis and comprising:
    a reservoir for containing a fluid composition, the reservoir comprising a top portion, a base portion opposing the top portion, and at least one sidewall extending between and connecting the top and base portions;
    a nozzle operatively connected with the reservoir, wherein the nozzle is in fluid communication with the reservoir for releasing the fluid composition; and
    an outer cover operatively connected with the reservoir, wherein the outer cover comprises a top and a skirt that extends from the top of the outer cover and at least partially overlaps with the sidewall of the reservoir along the longitudinal axis, wherein the top of the outer cover comprises an orifice, wherein an air flow path is formed between the outer cover and the reservoir and extends from the skirt to the orifice.

11. The cartridge of claim 10, wherein at least a portion of the air flow path extends axially.

12. The cartridge of claim 10 further comprising a die operatively connected with the reservoir, wherein the die comprises the nozzle.

13. The cartridge of claim 12, wherein the die comprises a heater.

14. The cartridge of claim 12, wherein the die comprises a piezoelectric crystal.

15. The cartridge of claim 10, wherein the air flow path is defined by a width extending between the outer cover and the reservoir, wherein the width is at least 2 millimeters.

16. The cartridge of claim 10, wherein the cartridge is electrically connectable with the microfluidic delivery system.

17. A cartridge for a microfluidic delivery system, the cartridge comprising:
    a reservoir containing a fluid composition to be dispensed from at least one nozzle, and
    an outer cover connected with the reservoir, the outer cover having a top with an orifice disposed adjacent to the nozzle and a skirt extending from the top, wherein at least one of the reservoir and the outer cover comprising electrical contacts that are electrically connectable with the microfluidic delivery system.

18. A microfluidic delivery system comprising:
    a housing having a base, at least one sidewall connected with the base, and an opening for receiving a cartridge at least partially within the housing, wherein the housing comprises an air inlet;
    a fan in fluid communication with the housing;
    a cartridge releasably and electrically connectable with the housing, wherein the cartridge has a longitudinal axis, the cartridge comprising a reservoir containing a fluid composition to be dispensed from at least one nozzle, and
    an outer cover connected with the reservoir, the outer cover having a top with an orifice disposed adjacent to the nozzle and an skirt extending from the top, the outer cover comprising an orifice that is disposed adjacent to the nozzle, wherein an air flow path is formed by a gap between the reservoir and the outer cover.

19. The microfluidic delivery system of claim 18, wherein when the cartridge is connected with the housing, the cartridge is in fluid communication with the housing.

20. The microfluidic delivery system of claim 18 further comprising a die in fluid communication with the reservoir, wherein the die comprises the nozzle and a heater for volatilizing the fluid composition.

* * * * *